US011065227B2

(12) United States Patent
Stott et al.

(10) Patent No.: US 11,065,227 B2
(45) Date of Patent: Jul. 20, 2021

(54) USE OF CANNABINOIDS IN THE TREATMENT OF MULTIPLE MYELOMA

(71) Applicant: GW Research Limited, Cambridge (GB)

(72) Inventors: Colin Stott, Cambridge (GB); Massimo Nabissi, Camerino (IT)

(73) Assignee: GW Research Limited, Cambridge (GB)

( * ) Notice: Subject to any disclaimer, the term of this patent is extended or adjusted under 35 U.S.C. 154(b) by 0 days.

(21) Appl. No.: 16/328,209

(22) PCT Filed: Jul. 31, 2017

(86) PCT No.: PCT/GB2017/052229
§ 371 (c)(1),
(2) Date: Feb. 25, 2019

(87) PCT Pub. No.: WO2018/037203
PCT Pub. Date: Mar. 1, 2018

(65) Prior Publication Data
US 2019/0175547 A1    Jun. 13, 2019

(30) Foreign Application Priority Data

Aug. 25, 2016 (GB) ..................... 1614522

(51) Int. Cl.
| | | |
|---|---|---|
| A61K 31/352 | (2006.01) | |
| A61K 31/05 | (2006.01) | |
| A61K 45/06 | (2006.01) | |
| A61K 31/69 | (2006.01) | |
| A61P 35/00 | (2006.01) | |
| A61K 38/07 | (2006.01) | |

(52) U.S. Cl.
CPC ............ *A61K 31/352* (2013.01); *A61K 31/05* (2013.01); *A61K 31/69* (2013.01); *A61K 38/07* (2013.01); *A61K 45/06* (2013.01); *A61P 35/00* (2018.01)

(58) Field of Classification Search
CPC ...... A61K 31/352; A61K 31/69; A61K 45/06; A61K 38/07; A61K 31/05; A61K 31/704; A61K 31/454; A61P 35/00
See application file for complete search history.

(56) References Cited

U.S. PATENT DOCUMENTS

| | | | |
|---|---|---|---|
| 6,403,126 B1 | 6/2002 | Webster | |
| 6,949,582 B1 | 9/2005 | Wallace | |
| 8,293,786 B2 | 10/2012 | Stinchcomb | |
| 8,673,368 B2 | 3/2014 | Guy et al. | |
| 9,017,737 B2 | 4/2015 | Kikuchi et al. | |
| 9,023,322 B2 | 5/2015 | Van Damme et al. | |
| 9,066,920 B2 | 6/2015 | Whalley et al. | |
| 9,095,554 B2 | 8/2015 | Lewis et al. | |
| 9,125,859 B2 | 9/2015 | Whalley et al. | |
| 9,168,278 B2 | 10/2015 | Guy et al. | |
| 9,259,449 B2 | 2/2016 | Raderman | |
| 9,474,726 B2 | 10/2016 | Guy et al. | |
| 9,522,123 B2 | 12/2016 | Whalley et al. | |
| 9,730,911 B2 | 8/2017 | Verzura et al. | |
| 9,949,936 B2 | 4/2018 | Guy et al. | |
| 9,949,937 B2 | 4/2018 | Guy et al. | |
| 9,956,183 B2 | 5/2018 | Guy et al. | |
| 9,956,184 B2 | 5/2018 | Guy et al. | |
| 9,956,185 B2 | 5/2018 | Guy et al. | |
| 9,956,186 B2 | 5/2018 | Guy et al. | |
| 10,092,525 B2 | 10/2018 | Guy et al. | |
| 10,111,840 B2 | 10/2018 | Guy et al. | |
| 10,137,095 B2 | 11/2018 | Guy et al. | |
| 2004/0049059 A1 | 3/2004 | Mueller | |
| 2004/0110828 A1 | 6/2004 | Chowdhury et al. | |
| 2005/0042172 A1 | 2/2005 | Whittle | |
| 2005/0266108 A1 | 12/2005 | Flockhart et al. | |
| 2006/0039959 A1 | 2/2006 | Wessling | |
| 2007/0060638 A1 | 3/2007 | Olmstead | |
| 2008/0119544 A1 | 5/2008 | Guy et al. | |
| 2008/0188461 A1 | 8/2008 | Guan | |
| 2009/0264063 A1 | 10/2009 | Tinsley et al. | |
| 2009/0306221 A1 | 12/2009 | Guy et al. | |
| 2010/0239693 A1 | 9/2010 | Guy et al. | |
| 2010/0317729 A1 | 12/2010 | Guy et al. | |
| 2011/0028431 A1 | 2/2011 | Zerbe et al. | |
| 2011/0038958 A1 | 2/2011 | Kikuchi et al. | |

(Continued)

FOREIGN PATENT DOCUMENTS

| | | |
|---|---|---|
| CA | 2737447 | 10/2012 |
| CA | 2859934 | 3/2016 |

(Continued)

OTHER PUBLICATIONS

[No Author Listed] "Cannabidiol Therapy for Aicardi Syndrome" Aug. 2014, 4 pages.
[No Author Listed], "Missouri House passes cannabis extract legislation," Kansas City Star, 2014, https://kansascity.com/news/politics-government/article346747.html, 2 pages.

(Continued)

*Primary Examiner* — Sahar Javanmard
(74) *Attorney, Agent, or Firm* — Cooley LLP

(57) ABSTRACT

The present invention relates to the use of a combination of tetrahydrocannabinol (THC) and cannabidiol (CBD) in the treatment of multiple myeloma. The combination of THC and CBD appears to be particularly effective in reducing cell viability and cell migration in this disease. Preferably the THC and CBD are used is in the form of a highly purified extract of *cannabis* such that the cannabinoids are present at greater than 98% of the total extract (w/w) and the other components of the extract are characterised. Alternatively, the THC and CBD may be a synthetically produced cannabinoid.

16 Claims, 8 Drawing Sheets

(56) References Cited

U.S. PATENT DOCUMENTS

| | | |
|---|---|---|
| 2011/0082195 A1 | 4/2011 | Guy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0202891 A1 | 8/2012 | Stinchcomb et al. |
| 2012/0270845 A1 | 10/2012 | Bannister et al. |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0320698 A1 | 11/2015 | Whalley et al. |
| 2015/0335590 A1 | 11/2015 | Whalley et al. |
| 2015/0343071 A1 | 12/2015 | Vangara |
| 2015/0359755 A1 | 12/2015 | Guy et al. |
| 2015/0359756 A1 | 12/2015 | Guy et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2016/0256411 A1 | 9/2016 | Aung-Din |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Whalley et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0083418 A1 | 3/2019 | Guy et al. |
| 2019/0167583 A1 | 6/2019 | Shah et al. |
| 2019/0175547 A1 | 6/2019 | Stott et al. |

FOREIGN PATENT DOCUMENTS

| | | |
|---|---|---|
| CN | 101040855 | 9/2007 |
| CN | 103110582 | 5/2013 |
| DE | 102012-105063 | 12/2013 |
| EP | 2448637 | 5/2012 |
| GB | 2384707 | 8/2003 |
| GB | 2434097 | 7/2007 |
| GB | 2434312 | 7/2007 |
| GB | 2450753 | 1/2009 |
| GB | 0911580.9 | 7/2009 |
| GB | 2456183 | 7/2009 |
| GB | 2471523 | 1/2011 |
| GB | 2478595 | 9/2011 |
| GB | 2479153 | 10/2011 |
| GB | 2471565 | 7/2012 |
| GB | 2478072 | 12/2012 |
| GB | 2478074 | 12/2012 |
| GB | 2492487 | 1/2013 |
| GB | 2487712 | 10/2015 |
| GB | 2531282 | 4/2016 |
| GB | 2438682 | 12/2017 |
| WO | WO 2002/064109 | 8/2002 |
| WO | WO 2003/099302 | 12/2003 |
| WO | WO 2004/016246 | 2/2004 |
| WO | WO 2004/016277 | 2/2004 |
| WO | WO 2006/054057 | 5/2006 |
| WO | WO 2006/133941 | 12/2006 |
| WO | WO 2007/083098 | 7/2007 |
| WO | WO 2007/138322 | 12/2007 |
| WO | WO 2008/019146 | 2/2008 |
| WO | WO 2008/094181 | 8/2008 |
| WO | WO 2008/129258 | 10/2008 |
| WO | WO 2008/144475 | 11/2008 |
| WO | WO 2008/021394 | 12/2008 |
| WO | WO 2008/146006 | 12/2008 |
| WO | WO 2009/007697 | 1/2009 |
| WO | WO 2009/007698 | 1/2009 |
| WO | WO 2009/020666 | 12/2009 |
| WO | WO 2010/012506 | 2/2010 |
| WO | WO 2011/001169 | 1/2011 |
| WO | WO 2011/121351 | 10/2011 |
| WO | WO 2012/033478 | 3/2012 |
| WO | WO 2012/093255 | 7/2012 |
| WO | WO 2013/032351 | 3/2013 |
| WO | WO 2014/146699 | 9/2014 |
| WO | WO 2015/142501 | 9/2015 |
| WO | WO 2015/184127 | 12/2015 |
| WO | WO 2015/193667 | 12/2015 |
| WO | WO 2015/193668 | 12/2015 |
| WO | WO 2016/059405 | 4/2016 |
| WO | WO 2016/084075 | 6/2016 |
| WO | WO 2016/118391 | 7/2016 |
| WO | WO 2016/147186 | 9/2016 |
| WO | WO 2016/022936 | 11/2016 |
| WO | WO 2016/199148 | 12/2016 |
| WO | WO 2017/168138 | 10/2017 |
| WO | WO 2018/002636 | 1/2018 |
| WO | WO 2018/002637 | 1/2018 |
| WO | WO/037203 | 3/2018 |

OTHER PUBLICATIONS

[No Author Listed], Cover and Table of Contents, J Pharmacology and Exp Therapeutics, Feb. 2010, 332(2), 4 pages.

Alger, "Not Too Excited? Thank Your Endocannabinoids," Neuron., Aug. 2006, 51(4):393-395.

American Epilepsy Society, Three Studies Shed New Light on the Effectiveness of Cannabis in Epilepsy, Oct. 14, 2014, 2 pages.

Ames et al., "Anticonvulsant effect of cannabidiol," S. Afr Med. J., Jan. 1986, 69(1):14.

Arain et al., "Pregabalin in the Management of Partial Epilepsy," Neuropsychiatr Dis Treat., Aug. 2009, 5:407-413.

Arslan and Tirnaksiz, "Self-emulsifying Drug Delivery Systems," Fabad J Pharm Sci, 2013,38(1):55-64.

Arzimanoglou et al., "All children who experience epileptic falls do not necessarily have Lennox-Gastaut syndrome . . . but many do," Epileptic Discord, 2011, 13:S3-S13.

AU Third Party Observations for Application No. AU2012314129, dated Mar. 19, 2015, 51 pages.

Avoli et al., "Cellular and molecular mechanisms of epilepsy in the human brain," Prog Neurobiol., 2005, 77(3):166-200.

Bakhsm, "Key Attributes of TKDL," Miftaah-al-Khazaain, 1930, 607-608 (with English translation).

Bancaud et al., "Proposal for Revised Clinical and Electroencephalographic Classification of Epileptic Seizures," Epilepsia, Aug. 1981, 22(4):489-501.

Banerjee et al., "Case Report: Aicardi syndrome: A report of five Indian cases," Neurology India, Mar. 2006, 54(1): 91-93.

Barker-Haliski et al, "How Clinical Development Can, and Should. Inform Translational Science," Neuron, Nov. 2014, 84: 582-593.

Benowitz et al., "Metabolic and Psychophysiologic studies of cannabidiol hexobarbital interaction," Clin Pharmacol Ther., 1980, 28(1):115-120.

Bertram, "The Relevance of Kindling for Human Epilepsy," Epilepsia, Apr. 2007, 48(Suppl. 2):65-74.

Bhatt et al., "Indigenous Plants in Traditional Healthcare System in Kedarnath Valley of Western Himalaya," Indian J Tradit Knowl., Apr. 2008, 7(2):300-310.

Bhattacharyya et al., "Modulation of mediotemporal and ventrostriatal function in humans by Delta9-tetrahydrocannabinol: a neural basis for the effects of *Cannabis sativa* on learning and psychosis," Arch Gen Psychiatry., 2009, 66:442-451.

BipolarHealthGroup.org [online], "Charlotte's Web Hemp Remedy," Bipolar Health Group, available on or before Sep. 6, 2017 ,

(56) References Cited

OTHER PUBLICATIONS retrieved on May 21, 2018, URL <http:/bipolarhealthgroup.org/index.php/charlottes-web-hemp-remedy/>, 6 pages.
Booth et al., "Legalization's opening of medical pot research is dream and nightmare," Denver Post, Dec. 14, 2013, retrieved on Feb. 8, 2017, URL <https://www.denverpost.com/2013/12/14/legalizations-opening-of-medical-pot-research-is-dream-and-nightmare/>, 6 pages.
Bostanci et al., "The effects of octanol on penicillin induced epileptiform activity in rats: An in vivo study," Epilepsy Res., Jul. 27, 2006, 71(2-3):188-194.
Braida et al., "Post-ischemic treatment with cannabidiol prevents electroencephalographic flattening, hyper locomotion and neuronal injury in gerbils" Neuroscience Letters., 2003, 346:61-64.
Brust et al., "Marijuana use and the risk of new onset seizures," Trans Am Clin Climatol Assoc., 1992, 103:176-181.
Carlini et al., "Hypnotic and Antiepileptic Effects of Cannabidiol," J Clin Pharmacol., Aug.-Sep. 1981, 21(8-9 Suppl):417S-427S.
Castel-Branco et al., "The Maximal Electroshock Seizure (MES) Model in the Preclinical Assessment of Potential New Antiepileptic Drugs," Methods Find Exp Clin Pharmacol., 2009, 31(2); 101-106.
Charlotte's Web [online], "When to Expect Results from CW Hemp Oil", Mar. 13, 2017, retrieved on May 21, 2018, URL https://www.cwhemp.com/blog/expecting-results-from-hemp, 6 pages.
Charlotte's Web [online], "Whole-Plant Cannabinoids Outperform Single Molecule Compounds," CWHemp.com, Jan. 11, 2017, retrieved on Jun. 16, 2017, URL <https://www.cwhemp.com/blog/whole-plant-cw-hemp-cannabinoids>, 5 pages.
ChildNeurologyFoundation.org [online], "Disorder Directory: Learn from the Experts—LGS (Lennon-Gastaut Syndrome)," Child Neurology Foundation, available on or before Sep. 6, 2005, retrieved on May 21, 2018, URL http://www.childneurologyfoundation.org/disorders/lgs-lennox-gastaut-syndrome, 10 pages.
Chiron and Dulac, "The Pharmacologic Treatment of Dravet Syndrome," Epilepsia, 2011, 52(Suppl. 2): 72-75.
Chiu et al., "The Influence of Cannabidiol and Δ9-Tetrahydrocannabinol on Cobalt Epilepsy in Rats," Epilepsia., 1979, 20:365-375.
Chou, "Theoretical basis, experimental design, and computerized simulation of synergism and antagonism in drug combination studies," Pharmacol Rev., Sep. 2006, 58(3), 621-681.
Conry et al., "Clobazam in the treatment of Lennox-Gastaut syndrome," Epilepsia, May 2009, 50(5):1158-1166.
Consroe and Sandyk, "Chapter 12: Potential Role of Cannabinoids for Therapy of Neurological Disorders," Marijuana / Cannabinoids: Neurobiology and Neurophysiology, ed. L. Murphy, 1992, 459-524.
Consroe et al., "Anticonvulsant drug antagonism of Δ$^9$tetrahydrocannabinol-induced seizures in rabbits," Res Commun Chem Pathol Pharmacol., Jan. 1977, 16(1):1-13.
Consroe et al., "Anticonvulsant Interaction of Cannabidiol and Ethosuximide in Rats," J. Pharm. Pharmac., Aug. 1977, 29(8):500-501.
Consroe et al., "Anticonvulsant Nature of Marihuana Smoking," JAMA, Oct. 1975, 234(3):306-307.
Consroe et al., "Cannabidiol—Antiepileptic Drug Comparisons and Interactions in Experimentally Induced Seizures in Rats," J. Pharm. Exp. Therap., Apr. 1977, 201(1):26-32.
Consroe et al., "Effects of Cannabidiol on Behavioral Seizures Caused by Convulsant Drugs or Current in Mice," Eur J Pharm, Sep. 1982, 83(3-4):293-298.
Consroe et al., "Chapter 2: Therapeutic Potential of Cannabinoids in Neurological Disorders," Cannabinoids as Therapeutic Agents, R. Mechoulam ed., 1986, 21-49.
Cortesi et al., "Potential therapeutical effects of cannabidiol in children with pharmacoresistant epilepsy," Med Hypotheses., 2007, 68(4):920-921.
Cortez and Snead, "Chapter 10: Pharmacologic Models of Generalized Absence Seizures in Rodents," Models of Seizures and Epilepsy, 2006, 111-126.

Crespel, et al., "Chapter 14: Lennox-Gastaut Syndrome," Epileptic Syndromes in Infancy, Childhood, and Adolescence, 2012, 5th Edition, ed. M. Bureau, 189-216.
Cunha et al., "Chronic Administration of Cannabidiol to Healthy Volunteers and Epileptic Patients," Pharmacology, 1980. 21(3):175-185.
Czapinski et al., "3-17-08: Randomized 36-month comparative study of valproic acid (VPA), phenytoin (PHT), phenobarbital (PB) and carbamazepine (CBZ) efficacy in patients with newly diagnosed epilepsy with partial complex seizures," J. Neurol. Sci., Sep. 1997, 150(1):S162-S163.
Dasa et al., "Key Attributes of TKDL: Ganja," Brhat Nighantu Ratnakara (Saligramanighantubhusanam), 1997, 6 pages (with English translation).
Davis and Ramsey, "Antiepileptic action of marihuana-active substances," Federation Proceedings., Mar. 1949, 8:284-285.
Davis et al., "A Predominant Role for Inhibition of the Adenylate Cyclase/Protein Kinase A Pathway in ERK Activation by Cannabinoid Receptor 1 in NIE-115 Neuroblastoma Cells," J Biol Chem., Dec. 2003, 278(49): 48973-48980.
De Meijer, "Chapter 5: The Chemical Phenotypes (Chemotypes) of Cannabis," Handbook of Cannabis, ed. Roger G. Pertwee, 2014, 89-110.
De Oliveira, et al., "Anticonvulsant activity of β-caryophyllene against pentylenetetrazol-induced seizures," Epilepsy Behav, Mar. 2016, 56:26-31.
Deshpande et al., "Cannabinoid CB1 Receptor Antagonists Cause Status Epilepticus-like Activity in the Hippocampal Neuronal Culture Model of Acquired Epilepsy," Neurosci Lett., Jan. 2007, 411: 11-16.
Devinsky et al., "Cannabidiol: Pharmacology and potential therapeutic role in epilepsy and other neuropsychiatric disorders," Epilepsia, 2014, 55(6):791-802.
Dravet, "The core Dravet syndrome phenotype," Epilepsia, Apr. 2011, 52(Suppl 2): 3-9.
Dreifus et al., "Proposal for Revised Clinical and Electroencephalographic Classification of Epileptic Seizures," Epilepsia, Aug. 1981, 22:489-501.
Dulac and Kaminska, "Use of Lamotrigine in Lennox-Gastaut and Related Epilepsy Syndromes," J. Child Neurolog., Nov. 1997, 12(S1): S23-S29.
Dulac et al., "Vigabatrin in Childhood Epilepsy," J. Child Neurolog., 1991, 6(S2): S30-S37.
Eadie, "Shortcomings in the current treatment of epilepsy," Expert Rev Neurother., Dec. 2012, 12(12): 1419-1427.
Eggers, "Temporal lobe epilepsy is a disease of faulty neuronal resonators rather than oscillators, and all seizures are provoked, usually by stress," Med Hypotheses, 2007, 69(6): 1284-1289.
ElSohly and Gul, "Chapter 1: Constituents of *Cannabis sativa*," Handbook of Cannabis, 2014, ed. Roger G. Pertwee, 3-22.
Engel et al., "Chapter 1: What Should be Modeled?," In Models Seizure Epilepsy., 2006, 14 pages.
Engel, "Report of the ILAE Classification Core Group," Epilepsia, 2006, 47(9):1558-1568.
EPO Annex to the Communication in Opposition for European Appln. No. 10734541.5, dated Jan. 28, 2016, 5 pages.
EPO Auxiliary Requests to the File in European Patent No. EP2448637, dated Nov. 2, 2016, 45 pages.
EPO Communication of a Notice of Opposition in European Appln. No. 10734541.5, dated Dec. 17, 2014, 1 page.
EPO Communication Pursuant to Article 94(3) EPC in European Appln. No. 10734541.5, dated Oct. 23, 2012, 3 pages.
EPO Interlocutory Decision in Opposition in European Appln. No. EP2448637, dated Dec. 15, 2016, 91 pages.
EPO Letter from Opponent Regarding Oral Proceedings in European Patent No. EP2448637, dated Oct. 20, 2016, 6 pages.
EPO Notice of Appeal in European Patent No. EP2448637, dated Feb. 14, 2017, 5 pages.
EPO Notice of Opposition to a European Patent No. EP2448637, dated Dec. 5, 2014, 20 pages.
EPO Opponent Response to the Preliminary Opinion of the Opposition Division in European Patent No. EP2448637, dated Jun. 23, 2016, 27 pages.

(56) References Cited

OTHER PUBLICATIONS

EPO Opponent Response to the Preliminary Opinion of the Opposition Division in European Patent No. EP2448637, dated Sep. 9, 2016, 25 pages.
EPO Opponent Response to the Written Submissions in European Patent No. EP2448637, dated Oct. 12, 2016, 18 pages.
EPO Opponent Response to the Written Submissions in European Patent No. EP2448637, dated Oct. 20, 2016, 3 pages.
EPO Opponent Written Submission in European Patent No. EP2448637, dated Nov. 4, 2016, 3 pages.
EPO Opposition, Expert Statement of Dr. Emma Louise Cheetham in European Appln. No. EP10734541.5, dated Nov. 4, 2016, 1 pages.
EPO Opposition, Expert Statement of Professor Anthony G Marson in European Appln. No. EP10734541.5, dated Jun. 14, 2016, 9 pages.
EPO Opposition, Expert Statement of Professor Benjamin J. Whalley in European Appln. No. EP10734541.5, dated Sep. 9, 2016, 11 pages.
EPO Opposition, Expert Statement of Vincenzo Di Marzo in European Appln. No. EP10734541.5, dated Sep. 9, 2016, 10 pages.
EPO Opposition, Supplemental Expert Statement of Professor Benjamin J. Whalley, dated Nov. 4, 2016, 9 pages.
EPO Reply of the Patent Proprietor to the Notice(s) of Opposition in European Patent No. 2448637, dated May 28, 2015, 12 pages.
EPO Reply to Examination Report in European Patent Application No. 10734541.5, dated Feb. 15, 2013, 54 pages.
EPO Reply to Opponent's Written Submission in European Patent No. EP2448637, dated Nov. 4, 2016, 13 pages.
EPO Reply to Opponent's Written Submissions in European Patent No. EP2448637, dated Oct. 18, 2016, 5 pages.
EPO Reply to Preliminary Opinion and Opponent's Observations in European Patent No. EP2448637, dated Sep. 9, 2016, 65 pages.
EPO Reply to Proprietor's Statement of Grounds of Appeal in European Patent No. EP2448637, dated Sep. 8, 2017, 5 pages.
EPO Response to the Statement of Grounds of Appeal in European Patent No. 2448637, dated Sep. 5, 2017, 17 pages.
EPO Statement of Grounds of Appeal in European Appln. No. 10734541.5, dated Apr. 21, 2017, 14 pages.
EPO Statement of Grounds of Appeal in European Appln. No. 10734541.5, dated Apr. 12, 2017, 6 pages.
EPO Statement of Opposition in European Appln. No. EP10734541.5, dated Dec. 5, 2014, 14 pages.
EPO Third Party Observations in European Appln. No. EP10734541.5, dated Apr. 3, 2017, 19 pages.
EPO Third Party Observations in European Appln. No. EP11712658.1, dated Nov. 22, 2013, 14 pages.
Fariello, "Parenteral Penicillin in Rats: An Experimental Model of Multifocal Epilepsy," Epilepsia, 1976, 17:217-222.
FDA [online], "Warning Letters and Test Results for Cannabidiol-Related Products," 2015 Warning Letters, retrieved on Nov. 14, 2017, URL <https://www.fda.gov/newsevents/publichealthfocus/ucm484109.htm>, 4 pages.
FDA [online], "Warning Letters and Test Results for Cannabidiol-Related Products," 2016 Warning Letters, retrieved on Nov. 14, 2017, URL <https://www.fda.gov/newsevents/publichealthfocus/ucm484109.htm> , 4 pages.
FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
Ferdinand et al., "Cannabis—Psychosis Pathway Independent of Other Types of Psychopathology," Schizophrenia Research, 2005, 79:289-295.
Fisher et al., "The impact of epilepsy from the patient's perspective I. Descriptions and subjective perceptions," Epilepsy Research, 2000, 41(1):39-51.
Gabor et al., "Lorazepam Versus Phenobarbital: Candidates for Drug of Choice for Treatment of Status Epilepticus," J Epilepsy, Jan. 1990, 3(1):3-6.
Gallily et al., "Overcoming the Bell-Shaped Dose-Response of Cannabidiol by Using Cannabis Extract Enriched in Cannabidiol," Pharmacology & Pharmacy, Jan. 2015, 6:75-85.
Gardner [online], "Comes Now Epidiolex (FDA Approves IND Studies of CBD)," BeyondTHC.com, Oct. 22, 2013, retrieved on Jan. 31, 2018, URL <http://www.beyondthc.com/comes-now-epidiolex-fda-approves-ind-studies-of-cbd>, 4 pages.
Gastaut., "Clinical and Electroencephalographical Classification of Epileptic Seizures," Epilepsia, 1970, 11:102-113.
GB Combined Search and Examination Report in GB Appln. No. GB1116789.7, dated Jan. 4, 2012, 8 pages.
GB Combined Search and Examination Report in Application No. GB1611544.6, dated Mar. 29, 2017, 8 pages.
GB Combined Search and Examination Report in GB Appln. No. GB1100043.7, dated Mar. 25, 2011, 8 pages.
GB Combined Search and Examination Report in GB Appln. No. GB1121919.3, dated Feb. 29, 2012, 8 pages.
GB Combined Search and Examination Report in GB Appln. No. GB1410771.8, dated Feb. 27, 2015, 7 pages.
GB Combined Search and Examination Report in GB Appln. No. GB1414813.4, dated Sep. 5, 2014, 8 pages.
GB Combined Search and Examination Report in GB Appln. No. GB1418166.3, dated Jul. 2, 2015, 8 pages.
GB Combined Search and Examination Report in GB Appln. No. GB1418170.5, dated Jul. 2, 2015, 6 pages.
GB Combined Search and Examination Report in GB Appln. No. GB1418171.3, dated Jun. 29, 2015, 8 pages.
GB Combined Search and Examination Report in GB Appln. No. GB1506550.1, dated Feb. 5, 2016, 9 pages.
GB Combined Search and Examination Report in GB Appln. No. GB1514079.1, dated May 4, 2016, 9 pages.
GB Combined Search and Examination Report in GB Appln. No. GB1605448.8, dated Jan. 12, 2017, 6 pages.
GB Examination Report in GB Appln. No. GB1100043.7, dated Mar. 18, 2014, 2 pages.
Gedde [online], "Clinical Experience with Cannabis in Treatment-Resistant Pediatric Epilepsy," Marijuana for Medical Professionals Conference, Sep. 9-11, 2014, URL <http://www.theroc.us/images/gedde_presentation.pdf, Sep. 9-11, 2014>, 45 pages.
Gedde et al., "3.330: Whole Cannabis Extract of High Concentration Cannabidiol May Calm Seizures in Highly Refractory Pediatric Epilepsies," American Epilepsy Society, Dec. 2013, 449-450.
Geffrey et al., "Cannabidiol (CBD) Treatment for Refractory Epilepsy," American Epilepsy Society, Annual Meeting Abstract 2.427, 2014, retrieved on Feb. 10, 2017, URL <https://www.aesnet.org/meetings_events/annual_meeting_abstracts/view/1868979>, 2 pages.
Green [online], "CBD: An Unconventional Therapy," Nugs.com, Mar. 24, 2014, URL <http://nugs.com/article/cbd-an-unconventional-therapy.html>, 5 pages.
Gresham et al., "Treating Lennox-Gastaut syndrome in epileptic pediatric patients with third generation rufinamide," Neuropsychiatr Dis Treat, Oct. 5, 2010, 6:639-645.
Gross et al., "Marijuana use and Epilepsy: Prevalence in Patients of a Tertiary Care Epilepsy Center," Neurology, Jun. 8, 2004, 62(11):2095-2097.
Guerrini et al., "Lamotrigine and Seizure Aggravation in Severe Myoclonic Epilepsy," Epilepsia, 1998, 39(5):508-512.
Guimaraes et al., "Antianxiety effect of cannabidiol in the elevated plus-maze," Psychopharmacology, 1990, 100: 558-559.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL <https://www.gwpharm.com/about-us/news/gw-pharmaceuticals-announces-epidiolex%C2%AE-receives-fast-track-designation-fda-treatment>, 2 pages.
GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL <https://www.gwpharm.com/about-us/news/gw-pharmaceuticals-announces-physician-reports-epidiolex%C2%AE-treatment-effect-children>, 8 pages.

(56) References Cited

OTHER PUBLICATIONS

GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL <https://www.gwpharm.com/about-us/news/gw-pharmaceuticals-announces-preliminary-results-phase-2a-study-its-pipeline-compound>, 5 pages.
GWPharm [online], "GW Pharmaceuticals Provides Update on Orphan Program in Childhood Epilepsy for Epidiolex®," GW Pharmaceuticals Press Release, Nov. 15, 2013, retrieved on Jun. 20, 2018, URL <https://www.gwpharm.com/about-us/news/gw-pharmaceuticals-provides-update-orphan-program-childhood-epilepsy-epidiolex%C2%AE>, 5 pages.
GWPharm [online], "GW Pharmaceuticals Receives Orphan Drug Designation by FDA for Epidiolex® in the Treatment of Lennox-Gastaut Syndrome," GW Pharmaceuticals Press Release, Feb. 28, 2014, retrieved on Feb. 10, 2017, URL <https://www.gwpharm.com/about-us/news/gw-pharmaceuticals-receives-orphan-drug-designation-fda-epidiolex%C2%AE-treatment-lennox>, 4 pages.
GWPharm [online], "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release, Nov. 15, 2013, retrieved on Feb. 10, 2017, URL <https://www.gwpharm.com/about-us/news/gw-pharmaceuticals-provides-update-orphan-program-childhood-epilepsy-epidiolex%C2%AE>, 5 pages.
Heinemann et al., "Chapter 4: An Overview of In Vitro Seizure Models in Acute and Organotypic Slices," Models of Seizures and Epilepsy, 2006 35-44.
Hill et al., "$\Delta^9$-Tetrahydrocannabivarin suppresses in vitro epileptiform and in vivo seizure activity in adult rats," Epilepsia, Aug. 2010, 51(8):1522-1532.
Hill, "Cannabidivarin-rich cannabis extracts are anticonvulsant in mouse and rat via a CB1 receptor-independent mechanism," British Journal of Pharmacology, Oct. 2013, 170(3): 679-692.
Holmes et al. "Choosing the Correct AED: From Animal Studies to the Clinic," Pediatr Neurol, Mar. 2008, 38(3): 151-162.
Iannotti et al., "Nonpsychotropic plant cannabinoids, cannabidivarin (CBDV) and cannabidiol (CBD), activate and desensitize transient receptor potential vanilloid 1 (TRPV1) channels in vitro: Potential for the treatment of neuronal hyperexcitability," ACS Chem. Neurosci., Jul. 16, 2014, 5:1131-1141.
ICE Epilepsy Alliance, The Dravet Syndrome Spectrum, Nov. 2008, 2 pages.
*Insys Development Company, Inc.* v. *GW Pharma Limited and Otsuka Pharmaceutical Co., Ltd.,* Decision in IPR2017-00503, U.S. Pat. No. 9,066,920, dated Jul. 7, 2017, 26 pages.
*Insys Development Company, Inc.* v. *GW Pharma Limited and Otsuka Pharmaceutical Co., Ltd.,* Declaration by Mark Polyakov, IPR2017-00503, U.S. Pat. No. 9,066,920, dated May 29, 2018, 1 page.
*Insys Development Company, Inc.* v. *GW Pharma Limited and Otsuka Pharmaceutical Co., Ltd.,* Declaration of Professor Anthony G. Marson in IPR2017-00503, U.S. Pat. No. 9,066,920, dated Dec. 13, 2016, 28 pages.
*Insys Development Company, Inc.* v. *GW Pharma Limited and Otsuka Pharmaceutical Co., Ltd.,* Declaration of Professor H. Steve White in IPR2017-00503, U.S. Pat. No. 9,066,920, dated Oct. 24, 2017, 69 pages.
*Insys Development Company, Inc.* v. *GW Pharma Limited and Otsuka Pharmaceutical Co., Ltd.,* Declaration of Professor Leslie Benet in IPR2017-00503, U.S. Pat. No. 9,066,920, dated Nov. 22, 2016, 18 pages.
*Insys Development Company, Inc.* v. *GW Pharma Limited and Otsuka Pharmaceutical Co., Ltd.,* Deposition of H. Steve White, dated Dec. 13, 2016, 50 pages.
*Insys Development Company, Inc.* v. *GW Pharma Limited and Otsuka Pharmaceutical Co., Ltd.,* Final Written Decision in IPR2017-00503, U.S. Pat. No. 9,066,920, dated Jan. 3, 2019, 40 pages.
*Insys Development Company, Inc.* v. *GW Pharma Limited and Otsuka Pharmaceutical Co., Ltd.,* Patent Owners' Preliminary Response in IPR2017-00503, U.S. Pat. No. 9,066,920, dated Apr. 11, 2017, 45 pages.
*Insys Development Company, Inc.* v. *GW Pharma Limited and Otsuka Pharmaceutical Co., Ltd.,* Petition for Inter Partes Review, IPR2017-00503, U.S. Pat. No. 9,066,920, dated Dec. 16, 2016, 78 pages.
*Insys Development Company, Inc.* v. *GW Pharma Limited and Otsuka Pharmaceutical Co., Ltd.,* Petitioner's Brief Regarding Ground III of the IPR, IPR2017-00503, U.S. Pat. No. 9,066,920, dated May 29, 2018, 45 pages.
*Insys Development Company, Inc.* v. *GW Pharma Limited and Otsuka Pharmaceutical Co., Ltd.,* Petitioner's Reply to Patent Owner's Response, IPR2017-00503, U.S. Pat. No. 9,066,920, dated Jun. 19, 2018, 6 pages.
*Insys Development Company, Inc.* v. *GW Pharma Limited and Otsuka Pharmaceutical Co., Ltd.,* Petitioner's Reply to Response in IPR2017-00503, U.S. Pat. No. 9,066,920, dated Jan. 19, 2018, 36 pages.
IUPHAR/BPS Guide to Pharmacology [online], "Entry for $\Delta 9$-tetrahydrocannabidiol," available on or before Mar. 29, 2016, retrieved on Jun. 20, 2018, URL <http://www.guidetopharmacology.org/GRAC/LigandDisplayForward?tab=biology&ligandId=242>, 2 pages.
Iuvone et al., "Neuroprotective Effect of Cannabidiol, a Non-psychoactive Component From *Cannabis sativa*, on β-amyloid-induced toxicity in PC12 Cells," J Neurochem, Apr. 2004, 89(1):134-41.
Izzo et al., "Non-psychotropic plant cannabinoids: new therapeutic opportunities from an ancient herb," Trends in Pharmacological Sciences, 2009, 30(10):515-527.
Jacobson and Porter, "Survey of Current Cannabidiol Use in Pediatric Treatment-Resistant Epilepsy", Apr. 2013, URL <https://www.thcint.com/uploads/1/9/3/7/19371199/cannabidiol_use_in_pediatric_epilepsy.pdf>, 1 page.
Jeavons et al., "Sodium Calproate in Treatment of Epilepsy," Br Med J., Jun. 15, 1974, 2(5919):584-586.
Jones et al. [online], Info & Metrics / Article Information,"Cannabidiol Displays Antiepileptiform and Antiseizure Properties in Vitro and in Vivo," J Pharmacol Exp Ther., Feb. 2010, 332(2):569-577, retrieved on Jun. 25, 2018, URL: http://jpet.aspetjournals.org/content/332/2/569/tab-article-info, 9 pages.
Jones et al., "Cannabidiol Displays Antiepileptiform and Antiseizure Properties in Vitro and in Vivo," J Pharmacol Exp Ther., Feb. 2010, 332(2):559-577.
Joy et al., "Marijuana and Medicine: Assessing the Science Base", Institute of Medicine, National Academy Press, 1999, 170 pages.
Kahan et al., "Risk of Selection Bias in Randomized Trials," Trials, Sep. 2015, 16:405, 7 pages.
Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.
Karler et al., "The Cannabinoids as Potential Antiepileptics," J Clin Pharmacol., Aug.-Sep. 1981, 21:437S-448S.
Kelley et al., "Doose syndrome (myoclonic-astatic epilepsy): 40 years of progress," Developmental Medicine & Child Neurology, Aug. 2010, 52: 988-993.
Khan et al., "Key Attributes of TKDL: Laooq-e-Qinnab/Barai Zeequn-Nafs," Khazaain-al-Advia, 1911, 2 pages (with English translation).
Khan et al., "Key Attributes of TKDL: Nuskha-e-Qutoor," Muheet-e-Azam, 1887, 2 pages (with English translation).
Khan et al., "Key Attributes of TKDL: Sufoof-e-qinnab Barae Waja," Khazaain-al-Adiva, 1911, 5 pages (with English translation).
Khan et al., "Key Attributes of TKDL: Usaara-e-Qinnab Barai Qoolanj," Khazaain-al-Advia, 1911, 6 pages (with English translation).
Khan et al., "Key Attributes of TKDL: Zimad-e-qinnab," Khazaain-al-Adiva, 1911, 5 pages (with English translation).

(56) References Cited

OTHER PUBLICATIONS

Klitgaard et al., "Electrophysiological, neurochemical and regional effects of levetiracetam in the rat pilocarpine model of temporal lobe epilepsy," Seizure, Mar. 2003, 12(2):92-100.
Klitgaard et al., "Evidence for a unique profile of levetiracetam in rodent models of seizures and epilepsy," European J Pharm, Jul. 1998, 353(2):191-206.
Kramer et al., "Febrile infection-related epilepsy syndrome (FIRES): pathogenesis, treatment, and outcome: a multicenter study on 77 children," Epilepsia, Nov. 2011, 52(11):1956-1965.
Kuhn et al., "Potent activity of carfilzomib, a novel, irreversible inhibitor of the ubiquitin-proteasome pathway, against preclinical models of multiple myeloma," Blood, Nov. 2007, 110(9): 3281-3290.
Kwan et al., "Definition of drug resistant epilepsy: consensus proposal by the ad hoc Task Force of the ILAE Commission on Therapeutic Strategies," Epilepsia, Jun. 2010, 51(6):1069-1077.
LeafScience.com [online], "What are the Highest CBD Strains?" Oct. 15, 2014, retrieved on Feb. 16, 2017, URL <www.leafscience.com/2014/10/15/highest-cbd-strains/>, 2 pages.
Leo et al., "Cannabidiol and epilepsy: Rationale and therapeutic potential," Pharamacological Research, Mar. 2016, 107: 85-92.
Lewis, "Mystery Mechanisms," TheScientist.com, Jul. 29, 2016, retrieved on Nov. 8, 2017, URL <https://www.the-scientist.com/?articles.view/articleNo/46688/title/Mystery-Mechanisms/>, 2 pages.
Lieu et al., "Assessment of self-selection bias in a pediatric unilateral hearing loss study," Otolaryngol Head Neck Surg, Mar. 2010, 142(3): 427-433.
Lindamood and Colasanti, "Effects of $\Delta^9$-Tetrahydrocannabinol and Cannabidiol on Sodium-Dependent High Affinity Choline Uptake in the Rat Hippocampus1," J Pharmacology Experimental Therapeutics, 1980, 213(2):216-221.
Long et al., "The Pharmacological actions of cannabidiol," Drugs of the Future, Jul. 2005, 30(7):747-753.
Löscher and Schmidt, "Modern antiepileptic drug development has failed to deliver: ways out of the current dilemma." Epilepsia, Apr. 2011, 52(4):657-78.
Lowenstein "Chapter 363: Seizures and Epilepsy," Diseases of the Central Nervous System, 2008, 2498-2512.
Luttjohann et al., "A Revised Racine's scale for PTZ-induced seizures in rats," Physiology & Behavior, 2009, 98:579-586.
Lutz, "On-demand activation of the endocannabinoid system in the control of neuronal excitability and epileptiform seizures," Biochemical Pharmacology, Nov. 2004, 68(9):1691-1698.
Maa et al., "The Case for Medical Marijuana in Epilepsy," Epilepsia, Jun. 2014, 55(6):783-786.
Mackie, "Cannabinoid Receptors as Therapeutic Targets," Annu Rev Pharmacol Toxicol, 2006, 46:101-122.
Majoosi et al., "Key Attributes of TKDL: Saoot Baraae Sara," Kaamil-al-Sena'ah, Central Council for Research in Unani Medicine, 2005, 2 pages (with English translation).
Malfait et al., "The nonpsychoactive cannabis constituent cannabidiol is an oral anti-arthritic therapeutic in murine collagen-induced arthritis," PNAS, Aug. 15, 2000, 97(17):9561-9566.
Manni et al., "Obstructive Sleep Apnea in a Clinical Series of Adult Epilepsy Patients: Frequency and Features of the Comorbidity," Epilepsia, Jun. 2003, 44(6): 836-840.
Manno, "Status Epilepticus: Current Treatment Strategies," The Neurohospitalist, Jan. 2011, 1(1):23-31.
Mares et al., "Chapter 12: Electrical Stimulation-Induced Models of Seizures," Model of Seizures and Epilepsy, Asla Pitkänen, Philip A. Schwartzkroin & Solomon L. Moshéé, eds., 2004, 153-159.
Martin et al., "Structure-Anticonvulsant Activity Relationships of Cannabidiol Analogs," National Institute on Drug Abuse, Research Monograph Series, 1987, 79:48-58.
Mattson et al., "Comparison of carbamazepine, phenobarbital, phenytoin, and primidone in partial and secondarily generalized tonic-clonic seizures," N Engl J Med, Jul. 18, 1985, 313(3):145-151.
Mattson et al., "Prognosis for total control of complex partial and secondary generalized tonic clonic seizures," Neurology, 1996, 47:68-76.
McCormick et al., "On the Cellular Network Bases of Epileptic Seizures," Annu Rev Physiol, 2001, 63:815-846.
McNamara, "Chapter 19: Pharmacotherapy of the Epilepsies,", Goodman & Gilman's The Pharmacological Basis of Therapeutics 11th ed., McGraw-Hill Companies, 2006, 501-525.
Mechoulam et al., "Cannabidiol: An Overview of Some Pharmacological Aspects," J Clin Pharmacol, 2002, 42:11S-19S.
Mechoulam et al., "Toward drugs derived from cannabis," Naturwissenschaften, Apr. 1978, 65(4):174-179.
Medicos [online], "Convulsive Disorders and Their Interference with Driving," Medicos, 2014, retrieved Feb. 10, 2017, URL <https://www.medicosporlaseguridadvial.com/en/clinical-subjects/neurologic-diseases/convulsive-disorders-and-their-interference-with-driving/>, 3 pages.
Merlis, "Proposal for an International Classification of the Epilepsies," Epilepsia, 1970, 11:114-119.
Miller et al., "Mapping genetic modifiers of survival in a mouse model of Dravet syndrome," Genes, Brain and Behavior, 2014, 13:163-172.
Moral et al., "Pipeline on the Move," Drugs of the Future, Jan. 2014, 39(1): 49-56.
Morard et al., "Conversion to Sirolimus-Based Immunosuppression in Maintenance Liver Transplantation Patients," Liver Transplantation, 2007, 13:658-664.
Morelli et al., "The effects of cannabidiol and its synergism with bortezomib in multiple myeloma cell lines. A role for transient receptor potential Vanilloid type-2," Int J Cancer, Jun. 2014, 134(11):2534-2546.
MyVirtualMedicalCentre [online], "Aicardi syndrome," mvmc.com, Feb. 2004, retrieved on Jan. 25, 2019, https://www.myvmc.com/diseases/aicardi-syndrome/, 6 pages.
Nabissi et al, "Cannabinoids synergize with cafilzomib, reducing multiple myeloma cells viability and migration," Oncotarget, Oct. 2016, 7: 77553.
Neto et al., "The role of polar phytocomplexes on anticonvulsant effects of leaf extracts of Lippia Alba (Mill.) N.E. Brown chemotypes," J. Pharm Pharmacol, 2009, 61(7):933-939.
Ng et al., "Illicit Drug Use and the Risk of New-Onset Seizures," Am J Epidemiol, 1990, 132(1):47-57.
Oakley et al., "Dravet Syndrome Insights into pathophysiology and therapy from a mouse model of Dravet syndrome," Epilepsia, Apr. 2011, 52(Suppl. 2): 59-61.
Obay et al., "Antiepileptic effects of ghrelin on pentylenetetrazole-induced seizures in rats," Peptides, Jun. 2007, 28(6):1214-1219.
PCT International Preliminary Report on Patentability in International Appln. No. PCT/GB2010/051066, dated Jun. 9, 2011, 6 pages.
PCT International Preliminary Report on Patentability in International Appln. No. PCT/GB2012/052284, dated Dec. 12, 2013, 12 pages.
PCT International Preliminary Report on Patentability in International Appln. No. PCT/GB2015/051775, dated Aug. 10, 2016, 9 pages.
PCT International Preliminary Report on Patentability in International Appln. No. PCT/GB2015/053030, dated Apr. 18, 2017, 6 pages.
PCT International Preliminary Report on Patentability in International Appln. No. PCT/GB2016/051792, dated Sep. 1, 2017, 14 pages.
PCT International Preliminary Report on Patentability in International Appln. No. PCT/GB2017/052229, dated Feb. 26, 2019, 7 pages.
PCT International Preliminary Report on Patentability in International Appln. No. PCT/US2017/050868, dated Oct. 11, 2018, 7 pages.
PCT International Search Report and Written Opinion in International Appln. No. PCT/GB2010/051066 dated Dec. 13, 2010, 8 pages.

(56) References Cited

OTHER PUBLICATIONS

PCT International Search Report and Written Opinion in International Appln. No. PCT/GB2011/050649, dated May 30, 2011, 15 pages.
PCT International Search Report and Written Opinion in International Appln. No. PCT/GB2012/052284, dated Nov. 16, 2012, 11 pages.
PCT International Search Report and Written Opinion in International Appln. No. PCT/GB2015/051775, dated Aug. 26, 2015, 11 pages.
PCT International Search Report and Written Opinion in International Appln. No. PCT/GB2015/051776, dated Aug. 25, 2015, 11 pages.
PCT International Search Report and Written Opinion in International Appln. No. PCT/GB2016/052340, dated Oct. 25, 2016, 12 pages.
PCT International Search Report and Written Opinion in International Appln. No. PCT/GB2017/051913, dated Sep. 15, 2017, 9 pages.
PCT International Search Report and Written Opinion in International Appln. No. PCT/GB2017/051914, dated Sep. 12, 2017, 10 pages.
PCT International Search Report and Written Opinion in International Appln. No. PCT/GB2017/052229, dated Oct. 6, 2017, 10 pages.
PCT International Search Report and Written Opinion in International Appln. No. PCT/US2017/050868, dated Aug. 6, 2017, 14 pages.
PCT International Search Report and Written Opinion in International Appln. PCT/GB2017/051943, dated Sep. 12, 2017, 10 pages.
PCT International Search Report in International Appln. No. PCT/GB2012/050002, dated Feb. 24, 2012, 3 pages.
Pelliccia et al. [online], "Treatment with CBD in oily solution of drug-resistant paediatric epilepsies," 2005 Congress on Cannabis and the Cannabinoids, Leiden, The Netherlands: International Association for Cannabis as Medicine, 2005, 14, retrieved on Jun. 30, 2015, URL <http://www.cannabis-med.org/studies/ww_en_db_study_show.php?s_id=173&&search_pattern=EPILEPSY>, 2 pages, Abstract only.
Pereira et al., "Study pharmacologic of the GABAergic and glutamatergic drugs on seizures and status epilepticus induced by pilocarpine in adult Wistar rats," Neurosci Lett, Jun. 2007, 419(3):253-257.
Pertwee, "Cannabinoid receptor ligands clinical and neuropharmacological considerations, relevant to future drug discovery and development," Expert Opin Investig Drugs, Jul. 2000, 9(7): 1553-1571.
Pertwee, "Chapter 3: The Pharmacology and Therapeutic Potential of Cannabidiol," Cannabinoids, Ed Vincenzo Di Marzo ed., 2004, 32-83.
Pertwee, "The diverse CB1 and CB2 receptor pharmacology of three plant cannabinoids: Δ9-tetrahydrocannabinol, cannabidiol and Δ9-tetrahydrocannabivarin," Br. J. Pharmacol, 2008, 153(2):199-215.
Petrocellis et al., "Effects of cannabinoids and cannabinoid-enriched Cannabis extracts on TRP channels and endocannabinoid metabolic enzymes," British Journal of Pharmacology, 2011, 163:1479-1494.
Pohl et al., "Effects of flunarizine on Metrazol-induced seizures in developing rats," Epilepsy Res, 1987, 1:302-305.
Poortman-van der Meer, "A contribution to the improvement of accuracy in the quantitation of THC," Forensic Science International, Apr. 1999, 101(1): 1-8.
Porter et al., "Randomized, multicenter, dose-ranging trial of retigabine for partial-onset seizures," Neurology, Apr. 2007, 68(15): 1197-1204.
Porter et al., "Report of a Parent Survey of Cannabidiol-enriched Cannabis use in Pediatric Treatment-resistant Epilepsy," Epilepsy Behavior, Dec. 2013, 29(3): 574-577.
Potter, "Chapter 4: Cannabis Horticulture," Handbook of Cannabis, ed. Roger G. Pertwee, 2014, 65-88.
Pouton, "Lipid formulations for oral administration of drugs: non-emulsifying, self-emulsifying and 'self-microemulsifying' drug delivery systems," Eur. J Pharm Sci, Oct. 2000, 11(Supp. 2): S93-S98.
Press et al., "Parental reporting of response to oral cannabis extracts for treatment of refractory epilepsy," Epilepsy Behav, Apr. 2015, 45:49-52.
Pruitt et al., "Ethanol in Liquid Preparations Intended for Children," Padiatrics, Mar. 1984: 73(3): 405-407.
Raab et al., "Multiple myeloma," Lancet, Jul. 2009, 374(9686): 324-339.
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani et al., "Epilepsy in Aicardi-Goutieres syndrome," Official J Eur Paediatric Neurology Society, 2014, 18: 30-37.
Rauca et al., "The role of superoxide dismutase and a-tocopherol in the development of seizures and kindling induced by pentylenetetrazol—influence of the radical scavenger a-phenyl-N-tert-butyl nitrone," Brain Research, May 29, 2004, 1009(1-2):203-212.
Resstel et al., "5-$HT_{1A}$ receptors are involved in the cannabidiol-induced attenuation of behavioural and cardiovascular responses to acute restraint stress in rats," Br J Pharmacol, Jan. 2009, 156(1): 181-188.
Rosenberg et al., "Cannabinoids and Epilepsy," Neurotherapeutics, Oct. 2015, 12(4): 747-768.
Rosenkrantz et al., "Oral and Parenteral Formulations of Marijuana Constituents," J Pharm Sci, Jul. 1972, 61(7)1106-1112.
Rubio et al., "In Vivo Experimental Models of Epilepsy," Central Nervous System Agents in Medicinal Chemistry, 2010, 10:298-309.
Russo, "Taming THC: potential cannabis synergy and phytocannabinoid-terpenoid entourage effects," British J. of Pharm, 2011, 163:1344-1364.
Sadanandasarma et al., "Key Attributes of TKDL: Suddha Bhanga Visista Gunah Aur Matra," Rasatarangini 11th Ed., 1979:720-723 (with English translation).
SalutarisDrops.com [online], "Cannabidiol for Aicardi Syndrome," Salutaris, available on or before Oct. 2014, retrieved on Feb. 10, 2017, URL <http://web.archive.org/web/20141012220050/http://salutarisdrops.com/cannabidiol-aicardi-syndrome>, 3 pages.
Sander, "The epidemiology of epilepsy revisited," Curr Opin Neurol, Apr. 2003, 16(2):165-170.
Sastri et al., "Key Attributes of TKDL: Vijaya Kalpah (Apasmaranasaka)," Anandakandam 1st ed., 1952:241, 5 pages (with English translation).
Scuderi et al., "Cannabidiol in Medicine: A Review of its Therapeutic Potential in CNS Disorders," Phytother Res, May 2009, 23(5):597-602.
Shukla [online], "New Automated Purification Strategies for Scale-Up," PCISyntesis.com, posted Dec. 25, 2017, https://www.pcisynthesis.com/new-automated-purification-strategies-for-scale-up/, 5 pages.
Silva et al., "Clobazam as Add-on Therapy in Children with Epileptic Encephalopathy," Can J Neurol Sci, 2006 33: 209-213.
Sperling et al., "Carisbamate as adjunctive treatment of partial onset seizures in adults in two randomized, placebo-controlled trials," Epilepsia, Mar. 2010, 51(3):333-343.
Stafstrom et al., "Models of Pediatric Epilepsies: Strategies and Opportunities," Epilepsia, 2006, 47(8): 1407-1414.
Stephenson, "In Memoriam: Professor Jean Aicardi (1926-2015)," Pediatric Neurology, Jan. 2016, 54: 3-4.
Stott et al., "Cannabinoids for the pharmaceutical industry," Euphytica, 2004, 140:83-93.
Strickley, "Solubilizing Excipients in Oral and Injectable Formulations," Table VIII, Pharmaceutical Research, Feb. 2004, 21(2): 201-230.
Swann., "The Effects of Seizures on the Connectivity and Circuitry of the Developing Brain," MRDD, 2004, 10(2):96-100.
Thomas et al., "Evidence that the Plant Cannabinoid Δ9-Tetrahydrocannabivarin is a Cannabinoid CB1 and CB2 Receptor antagonist," Br J Pharmacol, Dec. 2005, 146(7):917-926.

(56) References Cited

OTHER PUBLICATIONS

Thumma et al., "Influence of plasticizers on the stability and release of a prodrug of Δ9-tetrahydrocannabinol incorporated in poly (ethylene oxide) matrices," Eur J Pharmceutics and Biopharmaceutics, Oct. 2008, 70(2): 605-614.
Thurman et al., "Standards for epidemiologic studies and surveillance of epilepsy," Epilepsia, Sep. 2011, 52 Suppl 7: 2-26.
Thurstone, "Avoid Charlotte's Web for Epilepsy," Jun. 26, 2014, URL <http://drthurstone.com/charlotted-web-not-safest-option-epiliepsy-treatment/>, 4 pages.
Trembly and Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract Only.
Turkanis et al., "An Electrophysiological Analysis of the Anticonvulsant Action of Cannabidiol on Limbic Seizures in Conscious Rats," Epilepsia, 1979, 20:351-363.
Unimed Pharmaceuticals, Inc., "Marinol®," Jul. 2006 <https://www.accessdata.fda.gov/drugsatfda_docs/label/2006/018651s025s0261b1.pdf>, 11 pages.
Usami et al., "Synthesis and Pharmacological Evaluation in Mice of Halogenated Cannabidiol Derivatives," Chem Pharm Bull, Nov. 1999, 47(11):1641-1645.
USPTO Decision on Appeal in U.S. Appl. No. 10/318,659 (Appeal 2009-011751), dated Jul. 8, 2010, 23 pages.
USPTO Decision on Appeal in U.S. Appl. No. 13/698,730 (Appeal 2016-006358), dated Jun. 21, 2017, 6 pages.
USPTO Information Disclosure Statement Form PTO-1449 in U.S. Appl. No. 13/380,305, dated Nov. 24, 2014, 8 pages.
USPTO Notice of Allowance in U.S. Appl. No. 13/380,305, dated Dec. 10, 2014, 5 pages.
USPTO Notice of Allowance in U.S. Appl. No. 13/380,305, dated Mar. 19, 2015, 7 pages.
USPTO Office Action in U.S. Appl. No. 13/380,305, dated Aug. 25, 2014, 6 pages.
USPTO Request for Continued Examination with the Amendment and Information Disclosure Statement in U.S. Appl. No. 13/380,305, filed Mar. 2, 2015, 8 pages.
USPTO Third Preliminary Amendment under 37 C.F.R. 1.115 in U.S. Appl. No. 13/380,305, dated May 23, 2014, 4 pages.
Utah.gov [online], "2nd Agenda Controlled Substances Advisory Committee Meeting," Nov. 12, 2013, URL <https://www.utah.gov/pmn/files/81459.pdf>, 63 pages.
Van Rijckevorsel, "Treatment of Lennox-Gastaut Syndrome: overview and recent findings," Neuropsychiatr Dis Treat, Dec. 2008, 4(6): 1001-1019.
Velasco et al., "Anticancer mechanisms of cannabinoids," Curr Oncol, Mar. 2016, 23(2): S23-S32.
Velisek, "Chapter 11: Models of Chemically-Induced Acute Seizures," Models of Seizures and Epilepsy, 2006, 127-152.
Veliskova, "Chapter 48: Behavioral Characterization of Seizures in Rats," Models Seizures Epilepsy, 2006, 601-611.
Vollner et al., "Haschisch XX+ [Haschiscc XX+]: Cannabidivarin, a new hashish substance," Tetrahedron Letters, 1969, 10(3):145-147.
Wahle et al., "Development of Tolerance to the Anticonvulsant Effect of Valproate but not to Ethosuximide in a Rat Model of Absence Epilepsy," Eur J Pharma, May 1990, 181(1-2): 1-8.
Wallace et al., "Assessment of the role of CB1 receptors in cannabinoid anticonvulsant effects," European J Pharmacology, 2001, 428(1):51-57.
Wallace et al., "Pharmacotherapy for Dravet syndrome," Pediatr. Drugs, Jun. 2016, 18:197-208.
Weston et al., "Tetrahydrocannabivarin Exhibits Anticonvulsant Effects in a Piriform Cortical Brain Slice Model of Epileptiform Activity," Proceedings of the British Pharm Society, Dec. 2006, retrieved on Mar. 1, 2017, URL <http://www.pA2online.org/abstract/abstract.jsp?abid=28533>, 1 page, Abstract Only.

Wikipedia.org [online], "Cannabinoid," Wikipedia, Apr. 2003, retrieved on Mar. 1, 2017, URL <https://en.wikipedia.org/wiki/Cannabinoid>, 15 pages.
Wingerchuk, "Cannabis for medical purposes: cultivating science, weeding out the fiction," Lancent, Jul. 2004, 364:315-316.
Yu et al., "Reduced sodium current in GABAergic interneurons in a mouse model of severe myoclonic epilepsy in infancy," Nature Neuroscience, Sep. 2006, 9(9): 1142-1149.
Yuriev, "Endogenic Cannabinoid System is a New Perspective Object of Pharmacotherapeutic Effect to Disease of Nervous System," Ukrainsky Metodichny Chasopis, 2005, 6(50): 21-29 (with English Abstract).
Zhao et al., "Chapter 27: Repetitive Seizures in the Immature Brain," Models of Seizures and Epilepsy, 2006, 341-350.
Zhornitsky and Potvin, "Cannabidiol in Humans—The Quest for Therapeutic Targets," Pharmaceuticals, 2012, 5:529-552.
Zuardi et al., "Cannabidiol, a *Cannabis sativa* constituent, as an antipsychotic drug," Brazilian Journal of Medicine and Biological Research, Apr. 2006, 39(4): 421-429.
Zuardi et al., "Cannabidiol: from an inactive cannabinoid to a drug with wide spectrum of action," Rev Bras Psiquiatr, 2008, 30(3): 271-80.
AU Re-examination report—standard patent for Australian Patent No. 2012204800, dated May 3, 2019, 7 pages.
Benowitz and Jones, "Cardiovascular and metabolic considerations in prolonged cannabinoid administration in man," J Clin Pharm, 1981, 21: 214S-223S.
cdc.gov [online], "2 to 20 years: Girls Stature-for-age and Weigh-for-age percentiles," National Center for Health Statistics and National Center for Chronic Disease Prevention and Health Promotion, last modified Nov. 2000, <https://www.cdc.gov/growthcharts/data/set1clinical/cj411022.pdf>, 1 page.
Consroe et al., "Controlled clinical trial of cannabidiol in Huntington's Disease," Pharmacology Biochemistry & Behavior, 1991, 40:701-708.
Curia et al., "The pilocarpine model of temporal lobe epilepsy," J Neuroscience Methods, Jul. 2008, 172(2-4): 143-157.
GB Combined Search and Examination Report in GB Appln. No. GB1621480.1, dated Sep. 22, 2017, pages.
Grotenhermen, "Epilepsiebehandlung des Angelman-Syndroms mit CBD (Cannabidiol) (Epilepsy treatment of Angelman syndrome with CBD (cannabidiol)," Angelman e.V., Jan. 2015, retrieved on Jun. 7, 2019, URL <http://s8a85e4d6fcfb04b6.jimcontent.com/download/version/1472724876/module/9873059694/name/Epilepsiebehandlung%20durch%20CBD.pdf>, 8 pages (with Machine translation).
Hill et al., "Cannabidivarin is anticonvulsant in mouse and rat," Br J Pharmacol, Dec. 2012, 167(8):1629-1642.
Karler et al., "The anticonvulsant activity of cannabidiol and cannabinol," Life Science, 1973, 13: 1527-1531.
Kruk-Slomka et al., "A comparison of mecamylamine and bupropion effects on memory-related responses induced by nicotine and scopolamine in the novel object recognition test in mice," Pharmacological Reports, Aug. 2014, 66(4): 638-646.
Kurz and Blass, "Use of dronabinol (delta-9-THC) in autism: a prospective single-case-study with an early infantile autistic child," 2010, Cannabinoids, 5(4): 4-6.
LaPrairie et al., "Cannabidiol is a negative allosteric modulator of the cannabinoid CB1 receptor," British J Pharmacology, 2015, 172(20): 4790-4805.
PCT Interntaional Search Report and Written Opinion in International Appln. No. PCT/GB2017/053735, dated Mar. 14, 2018, 14 pages.
Physician's Desk Reference, 63rd Ed., 2009, 423-431, 2192-2194, 2639-2242, 3019-3022.
Sandyk et al., "Preliminary trial of cannabidiol in Huntington's Disease," Marihuana: An International Research Report, 1988, 157-162.
Thomas et al., "Cannabidiol displays unexpectedly high potency as an antagonist of CB1 and CB2 receptor agonists in vitro," British J Pharmacology, 2007, 150(5): 613-623.
U.S. Department of Health and Human Services, Food and Drug Administration Center for Drug Evaluation and Research (CDER),

(56) References Cited

OTHER PUBLICATIONS

"Guidance for Industry Estimating the Maximum Safe Starting Dose in Initial Clinical Trials for Therapeutics in Adult Healthy Volunteers," Jul. 2005, 30 pages.
Zamberletti et al., "Alterations of prefrontal cortex GABAergic transmission in the complex psychotic-like phenotype induced by adolescent delta-9-tetrahydrocannabinol exposure in rats," Neurobiology of Disease, Mar. 2014, 63: 35-47.
U.S. Appl. No. 13/380,305, filed Mar. 19, 2012, Benjamin Whalley.
U.S. Appl. No. 14/579,061, filed Dec. 22, 2014, Benjamin Whalley.
U.S. Appl. No. 15/346,844, filed Nov. 9, 2016, Benjamin Whalley.
U.S. Appl. No. 16/149,983, filed Oct. 2, 2018, Benjamin Whalley.
U.S. Appl. No. 13/977,766, filed Jul. 1, 2013, Benjamin Whalley.
U.S. Appl. No. 14/345,968, filed Mar. 20, 2014, Benjamin Whalley.
U.S. Appl. No. 14/741,783, filed Jun. 17, 2015, Geoffrey Guy.
U.S. Appl. No. 15/284,766, filed Oct. 4, 2016, Geoffrey Guy.
U.S. Appl. No. 15/449,084, filed Mar. 3, 2017, Geoffrey Guy.
U.S. Appl. No. 15/449,124, filed Mar. 3, 2017, Geoffrey Guy.
U.S. Appl. No. 15/449,185, filed Mar. 3, 2017, Geoffrey Guy.
U.S. Appl. No. 15/449,204, filed Mar. 3, 2017, Geoffrey Guy.
U.S. Appl. No. 15/449,177, filed Mar. 3, 2017, Geoffrey Guy.
U.S. Appl. No. 15/948,412, filed Apr. 9, 2018, Geoffrey Guy.
U.S. Appl. No. 14/881,954, filed Oct. 13, 2015, Geoffrey Guy.
U.S. Appl. No. 14/881,969, filed Oct. 13, 2015, Geoffrey Guy.
U.S. Appl. No. 15/449,402, filed Mar. 3, 2017, Geoffrey Guy.
U.S. Appl. No. 15/449,535, filed Mar. 3, 2017, Geoffrey Guy.
U.S. Appl. No. 16/198,141, filed Nov. 21, 2018, Geoffrey Guy.
U.S. Appl. No. 14/741,829, filed Jun. 17, 2015, Geoffrey Guy.
U.S. Appl. No. 15/183,947, filed Jun. 16, 2015, Geoffrey Guy.
U.S. Appl. No. 15/519,233, filed Apr. 14, 2017, Geoffrey Guy.
U.S. Appl. No. 15/519,244, filed Apr. 14, 2017, Geoffrey Guy.
U.S. Appl. No. 15/640,033, filed Jun. 30, 2017, Jitinder Wilkhu.
U.S. Appl. No. 15/751,563, filed Feb. 9, 2018, Colin Stott.
U.S. Appl. No. 16/090,039, filed Sep. 28, 2018, Geoffrey Guy.
U.S. Appl. No. 16/314,583, filed Dec. 31, 2018, Stephen Wright.
U.S. Appl. No. 16/314,569, filed Dec. 31, 2018, Harshit Shah.
U.S. Appl. No. 16/467,639, filed Jun. 7, 2019, Geoffrey Guy.

The cytotoxic effects of THC and a THC-CBD combination are CB receptor and TRPV1 independent The effect of THC alone and a THC-CBD combination on sub-G1 phase in U266 and RPMI cell lines The effect of a THC-CBD combination on autophagic-cell death in MM cell lines The effect of a CBD-THC combination on necrosis The regulation of β5i subunit by a combination of THC-CBD in MM cell lines stimulated with IFN-γ

The effect of CFZ alone or in combination with a THC-CBD combination on cell viability The effect of a combination of THC, CBD and CFZ on cell migration in U266 cell line

USE OF CANNABINOIDS IN THE TREATMENT OF MULTIPLE MYELOMA

FIELD OF THE INVENTION

The present invention relates to the use of a combination of tetrahydrocannabinol (THC) and cannabidiol (CBD) in the treatment of multiple myeloma. The combination of THC and CBD appears to be particularly effective in reducing cell viability and cell migration in this disease.

Preferably the THC and CBD are used is in the form of a highly purified extract of *cannabis* such that the cannabinoids are present at greater than 98% of the total extract (w/w) and the other components of the extract are characterised. Alternatively, the THC and CBD may be a synthetically produced cannabinoid.

In use the combination of THC and CBD may be used concomitantly with one or more drugs used in the treatment of multiple myeloma. In particular the proteasome inhibitor carfilzomib appears to be particularly effective when used in concomitantly with the THC-CBD combination. The THC-CBD combination may be formulated for administration separately, sequentially or simultaneously with one or more concomitant drugs or the combination may be provided in a single dosage form. Where the THC-CBD combination is formulated for administration separately, sequentially or simultaneously it may be provided as a kit or together with instructions to administer the one or more components in the manner indicated. It may also be used as the sole medication, i.e. as a monotherapy.

BACKGROUND TO THE INVENTION

Multiple myeloma (MM), also known as myeloma, is a type of bone marrow cancer. MM is a malignant disorder characterized by uncontrolled monoclonal plasma cell proliferation and the accumulation of malignant plasma cells in the bone marrow, leading to anaemia, osteolytic bone lesions, renal insufficiency, hypercalcemia and finally to extramedullary disease (Raab et al. 2009). MM is different to leukaemia as it affects a different type of cell although both start in the bone marrow.

Multiple myeloma affects plasma cells inside the bone marrow. Myeloma cells divide and expand within the bone marrow, damaging the bones and affecting the production of healthy blood cells. Myeloma often affects many places in the body, whereby it is referred to as multiple myeloma. Commonly affected areas include the spine, skull, pelvis and ribs.

In the early stages of the disease, myeloma may not cause any symptoms. MM eventually causes a wide range of symptoms such as: persistent dull ache or specific areas of tenderness in bones; weak bones that fracture easily; tiredness, weakness and shortness of breath; anaemia; repeated infections; bruising and unusual bleeding.

MM is usually diagnosed from the detection of abnormal proteins produced by myeloma cells in the blood or urine of a patient.

MM is a rare form of cancer, with around 4,800 new cases diagnosed each year in the UK. There is currently no cure for MM, but treatment can often help control it for several years.

Treatment involves the use of anti-myeloma medications to destroy the myeloma cells. In addition the symptoms of bone pain, fractures and anaemia are also treated. MM is often relapsing and as such anti-myeloma medicines will be required to control the cancer when this occurs.

Patients diagnosed with MM may live less for than a year however approximately a third of patients may live for at least 10 years after diagnosis.

The medicines used to treat MM usually include chemotherapeutics, proteasome inhibitors such as bortezomib or carfilzomib, steroids and thalidomide.

Chemotherapeutic drugs used in MM include melphalan and cyclophosphamide. As with all chemotherapeutics the side effects associated with these drugs are an increased risk of infections, feeling sick, vomiting and hair loss.

Proteasome inhibitors such as bortezomib (BTZ) and carfilzomib (CFZ) are medications that can help kill myeloma cells by causing protein to build-up inside them. There are some limitations as to who can take these drugs.

Proteasome inhibitors block the action of proteasomes, which are cellular complexes that break down proteins. Multiple mechanisms are likely to be involved, but proteasome inhibition may prevent degradation of pro-apoptotic factors such as the p53 protein, permitting activation of programmed cell death in neoplastic cells dependent upon suppression of pro-apoptotic pathways.

Bortezomib causes a rapid and dramatic change in the levels of intracellular peptides. Proteasome inhibitors are being studied in the treatment of cancer, and three are approved for use in multiple myeloma: bortezomib, carfilzomib and ixazomib.

Although relatively effective in the treatment of multiple myeloma cells proteasome inhibitors have serious side effects including neutropenia, thrombocytopenia, peripheral neuropathy, fatigue, nausea, diarrhea, leukopenia, anemia, constipation, neuralgia, vomiting, lymphopenia, rash, pyrexia, and anorexia. These serious side effects often limit the amount of proteasome inhibitor that can be given to a patient and in consequence may be less effective.

Steroids such as corticosteroids are used to help destroy myeloma cells and make chemotherapy more effective. The two most common types used to treat myeloma are dexamethasone and prednisolone. Possible side effects include heartburn, indigestion, increased appetite, mood changes and problems falling asleep.

Thalidomide may also be used as this drug can help kill myeloma cells. This drug causes severe sleepiness and other side effects including constipation, dizziness, rashes and peripheral neuropathy. Thalidomide can also cause birth defects and increases the risk of developing a blood clot.

Another class of drugs which may additionally be used to treat MM are immunomodulatory drugs such as lenalidomide and pomalidomide.

Stem cell transplants may also be used after initial drug therapy outlined above. These are usually used after high doses of chemotherapy which affects healthy bone marrow. The stem cell transplant helps bone marrow recover.

It is common in MM for relapses to occur. Treatment for relapses is generally similar to the initial treatment, although non-intensive treatment is often preferred to further intensive treatment.

The symptoms and complications of MM are usually treated with painkillers, radiotherapy, bisphosphonate medication (to prevent bone damage and reduce the levels of calcium in the blood), blood transfusions or erythropoietin medication (to increase red blood cell count and treat anaemia), surgery (to repair or strengthen damaged bones, or treat compression of the spinal cord), dialysis (to treat kidney failure) and plasma exchange (to treat hyperviscosity).

There is growing evidence to support a role for cannabinoids in cancer therapy. Their effects in the induction of cell death, inhibition of proliferation and anti-metastatic activity in different human cancer in vitro and in vivo models (Velasco et al., 2016). The most relevant effect of cannabinoids in cancer, was investigated with tetrahydrocannabinol (THC) and cannabidiol (CBD). THC and CBD were able to reduce cell proliferation and induce autophagic-dependent cell death in glioblastoma (GBM), hepatocellular carcinoma, melanoma and breast cancer.

The cannabinoid CBD also has been shown to reduce viability, induce necrosis and to synergize with bortezomib (BTZ) in reducing cell proliferation and cell survival pathways in MM cell lines (Morelli et al. 2014).

The constitutive proteasome (cPTS) and the immunoproteasome (iPTS) are the two major isoforms of the proteasome that have been described in human. The cPTS s present in most cells and has different catalytic activities. During inflammatory states, the expression of these inducible 'immunosubunits' is strongly upregulated and the neosynthesis of cPTS is switched almost exclusively to the generation of the iPTS.

The cPTS has emerged as an important target in MM cancer therapy, leading to the approval of BTZ for newly diagnosed and relapsed/refractory MM. BTZ is a reversible cPTS inhibitor that inhibits cell cycle and induces apoptosis via regulation of the cyclin-dependent kinase (CDK) inhibitors, p21 and p27. BTZ displays hematologic toxicities (neutropenia and thrombocytopenia) and peripheral neuropathy. Therefore, to overcome these negative side effects and partially suppress BTZ resistance, a new generation of proteasome inhibitors was developed.

CFZ increases safety and efficacy in MM treatment and unlike BTZ, this drug creates irreversible adducts, specifically with the N-terminal threonine of the $\beta 5$ and $\beta 5 i$ subunits of cPTS and iPTS, respectively. CFZ also inhibits cell viability in different MM cell lines and patient-derived MM neoplastic cells by inducing apoptotic-signalling pathways.

Furthermore CFZ shows enhanced anti-MM activity compared with BTZ and it is also able to overcome resistance to BTZ in MM cells (Kuhn et al. 2007). Acquired resistance to BTZ, in MM, can be the result of the acquisition of mutations in the $\beta 5$ subunit and since the $\beta 5 i$ counterpart does not harbour similar mutations, the downregulation of iPTS in BTZ-resistant MM cell lines may provide a mechanism of escape.

In end-stage MM, malignant cells can survive and proliferate outside the microenvironment of the bone marrow. The chemokine receptor CXCR4 and the CD147 receptor, which are up regulated in MM plasma cells, have been shown to be involved in the recruitment of these cells to the bone marrow.

There are currently no data concerning the potential effects of cannabinoids in the regulation of iPTS activity and migration in MM. The present invention demonstrates the efficacy of a combination of THC and CBD either alone or in combination with CFZ, in regulating CFZ sensitivity, $\beta 5 i$ expression and MM cells migration.

BRIEF SUMMARY OF THE DISCLOSURE

In accordance with a first aspect of the present invention there is provided a combination of tetrahydrocannabinol (THC) and cannabidiol (CBD) for use in the treatment of multiple myeloma.

Preferably the THC and CBD further comprise one or more concomitant medications. The concomitant medications may be one or more of: a chemotherapeutic, a proteasome inhibitor; an immunomodulatory stimulator, a steroid or thalidomide.

More preferably the concomitant medication is a proteasome inhibitor. More preferably still the proteasome inhibitor is bortezomib, carfilzomib or ixazomib.

The therapeutically effective recommended dose of carfilzomib is 20 mg/m$^2$ IV, over 10 minutes, in Cycle 1 on Days 1 and 2. If this dose is tolerated, the dose is increased to the target dose of 27 mg/m$^2$ in Cycle 1 on Days 8, 9, 15, and 16, followed by a 12-day rest period (Days 17 to 28). Each 28-day period is considered one treatment cycle.

From Cycle 13 the Day 8 and 9 doses are omitted and therapy is discontinued after Cycle 18, however often unacceptable toxicity of carfilzomib occurs before this stage limiting the amount of proteasome inhibitor that can be given to a patient.

The ability to lower the effective dose of proteasome inhibitor would be greatly beneficial.

Preferably the dose of proteasome inhibitor is reduced relative to the dose prior to treatment with the THC and CBD.

Alternatively the dose of proteasome inhibitor is reduced relative to the therapeutically effective dose. This dose could be reduced to less than 27 mg/m$^2$ IV or less than 20 mg/m$^2$.

Preferably the THC and or CBD are present as a highly purified extract of *cannabis* which comprises at least 98% (w/w) of the particular cannabinoid. Alternatively the THC or CBD are present as synthetic compounds.

The dose of THC and/or CBD used may be from 0.1 to 1000 mg/kg/day.

Preferably the cannabinoids are present in a ratio of from 99:1 to 1:99 (THC:CBD). More preferably the cannabinoids are present in a ratio of from 10:1 to 1:10 (THC:CBD). More preferably the cannabinoids are present in a ratio of from 5:1 to 1:5 (THC:CBD). More preferably still the cannabinoids are present in a ratio of approximately 1:1 (THC:CBD).

In a further embodiment the amount of CBD present is greater than the amount of THC present. For example the ratio of THC:CBD is from 1:1 to 1:10 (THC:CBD) to 1:1 to 1:5 (THC:CBD) to 1:1 to 1:2 (THC:CBD).

In accordance with a second aspect of the present invention there is provided a method of treating multiple myeloma comprising administering a combination of tetrahydrocannabinol (THC) and cannabidiol (CBD) to a subject in need thereof.

Preferably the THC and CBD further comprises one or more concomitant medications, more preferably the concomitant medication is carfilzomib.

Preferably the subject is a human, more preferably a child or young adult.

In a further aspect of the invention the THC and CBD are provided in a composition suitable for use in the treatment of multiple myeloma. Said composition comprising THC and CBD and one or more pharmaceutically acceptable excipients.

The THC-CBD combination may be formulated for administration separately, sequentially or simultaneously with one or more concomitant drugs or the combination may be provided in a single dosage form. Where the THC-CBD combination is formulated for administration separately, sequentially or simultaneously it may be provided as a kit or together with instructions to administer the one or more components in the manner indicated. It may also be used as the sole medication, i.e. as a monotherapy.

DEFINITIONS

Definitions of some of the terms used to describe the invention are detailed below:

The cannabinoids described in the present application are listed below along with their standard abbreviations.

TABLE 4

Cannabinoids and their abbreviations

| | | |
|---|---|---|
| CBD | Cannabidiol | (structure) |
| THC | Tetrahydrocannabinol | (structure) |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *cannabis* plant. The phytocannabinoids can be isolated from plants to produce a highly purified extract or can be reproduced synthetically.

"Highly purified cannabinoid extracts" are defined as cannabinoids that have been extracted from the *cannabis* plant and purified to the extent that other cannabinoids and non-cannabinoid components that are co-extracted with the cannabinoids have been substantially removed, such that the highly purified cannabinoid is greater than or equal to 98% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

BRIEF DESCRIPTION OF THE DRAWINGS

Embodiments of the invention are further described hereinafter with reference to the accompanying drawings, in which.

LEGENDS TO THE FIGURES

Figure 1:
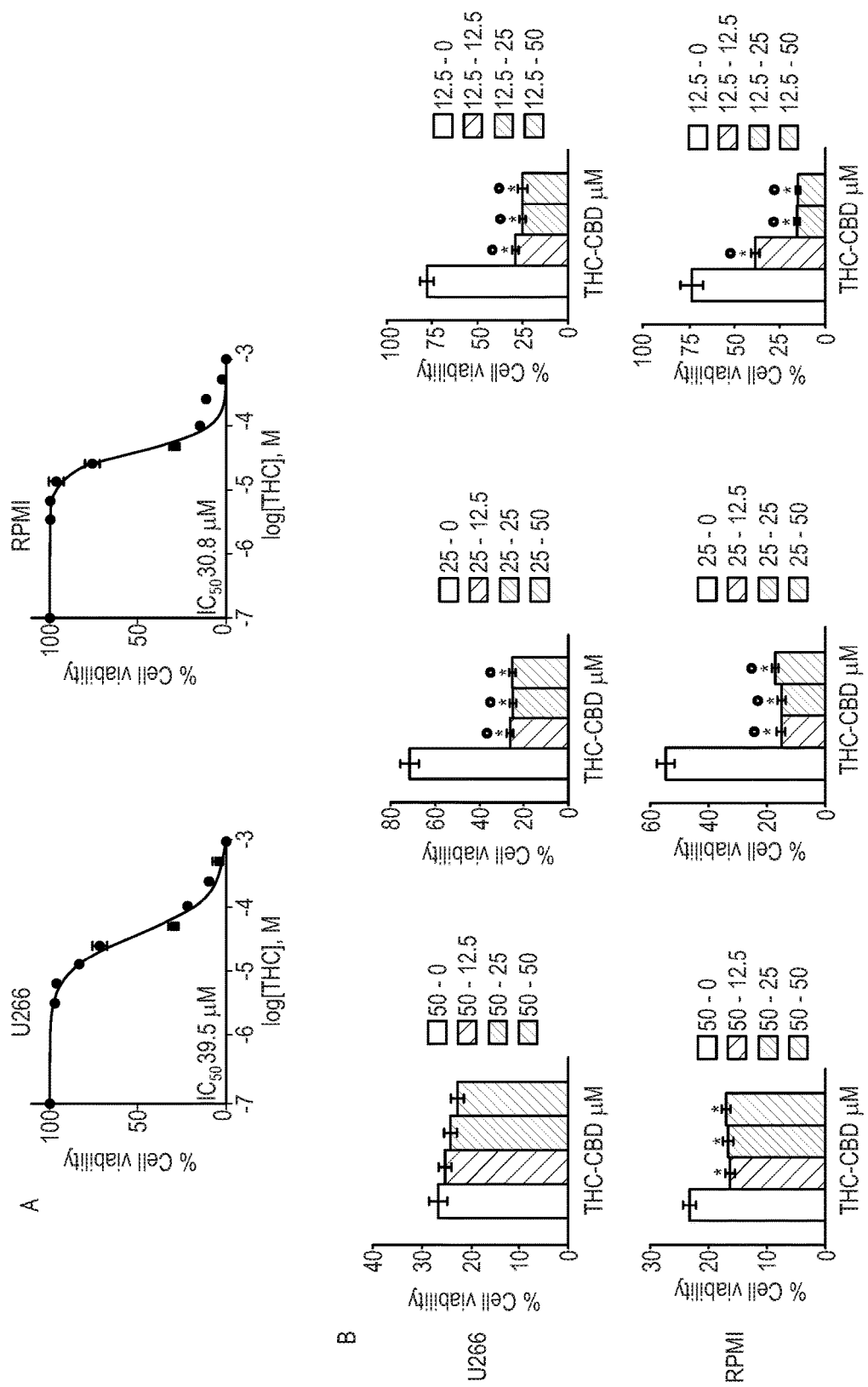
FIG. 1 shows the effect of THC alone and in combination with CBD on cytotoxicity in MM cell lines.

FIG. 1. (A) U266 and RPMI cell lines were treated with different doses of THC (from 0 to 1 mM). Cell viability was evaluated at 72 h post-treatments, by MTT assay. Data shown are expressed as mean±SE of three separate experiments. IC50 of THC in U266 and RPMI cell lines were indicated. (B) THC and CBD act synergistically in inducing cell cytotoxicity. U266 and RPMI cell lines were treated with different combination of THC (12.5-50 μM) and CBD (0-50 μM). Cell viability was evaluated at 72 h post-treatments, by MTT assay. Data shown are expressed as mean±SD of three separate experiments. *$p<0.05$ vs THC alone treated cells. ⊙ indicate synergism (C<1).

Figure 2:
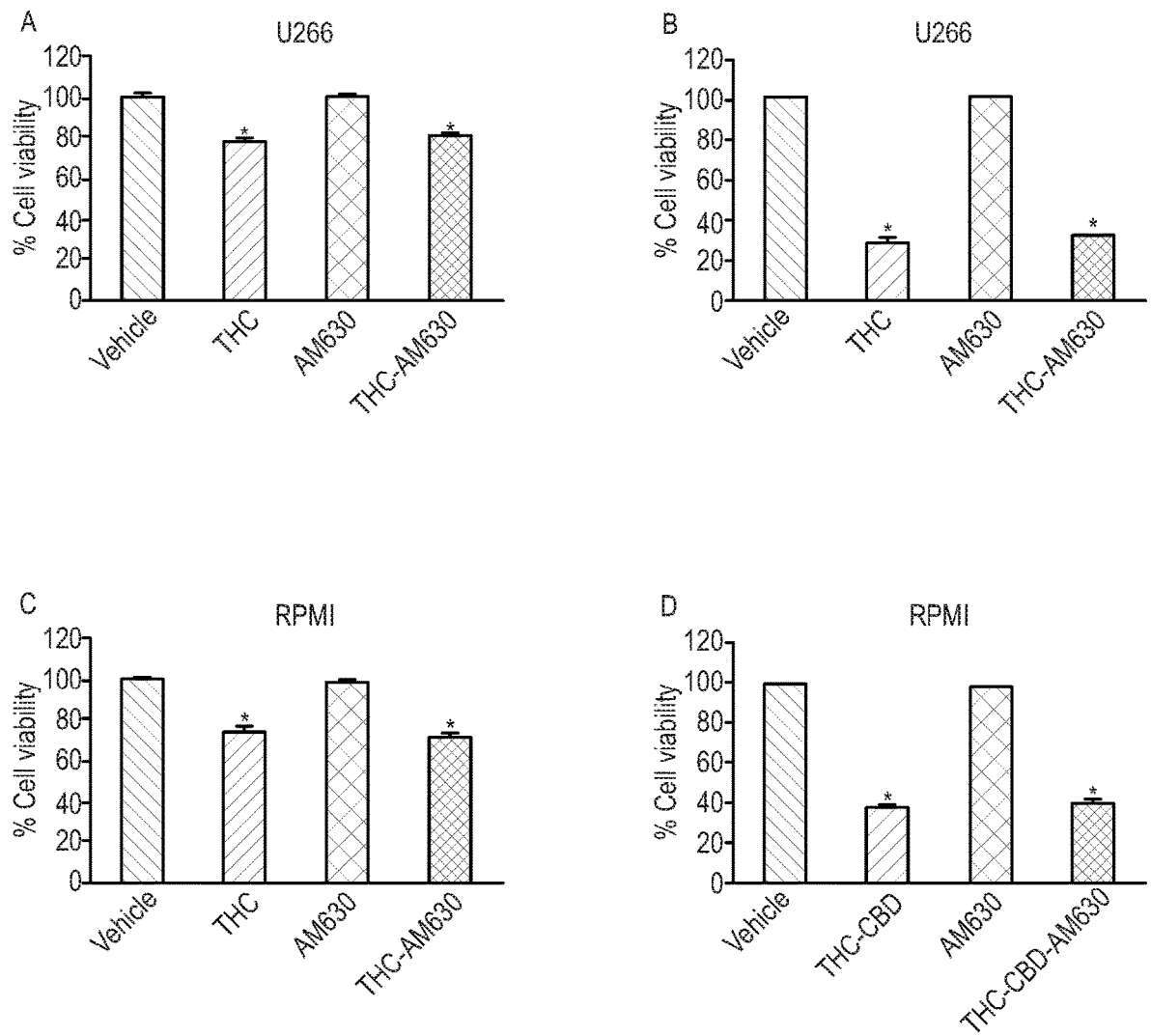
FIG. 2 shows the cytotoxic effects of THC and a THC-CBD combination are CB receptor and TRPV1 independent.

FIG. 2. U266 and RPMI cells were treated with AM630 (20 μM) alone or in combination with THC 12.5 μM (A, C), or with 12.5 μM CBD plus 12.5 μM THC (B, D). Cell viability was evaluated by MTT assay. Data shown are expressed as mean±SD of three separate experiments. *$p<0.05$ vs vehicle treated cells.

Figure 3:
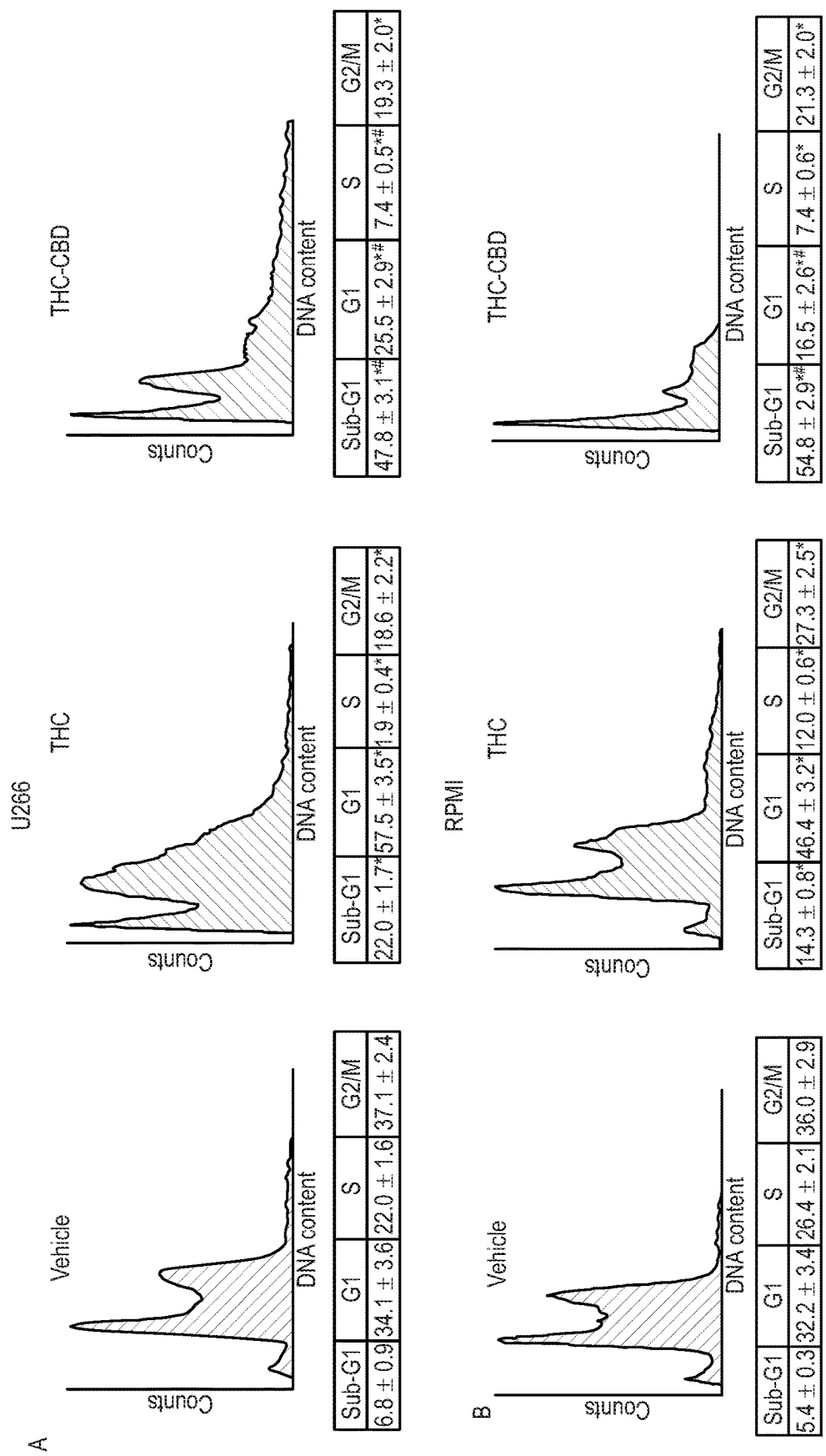
FIG. 3 shows the effect of THC alone and a THC-CBD combination on sub-G1 phase in U266 and RPMI cell lines.

FIG. 3. (A, B) Cell cycle analysis of U266 and RPMI cell lines treated with THC (12.5 μM) alone or in combination with CBD (12.5 μM). Cell cycle was performed by PI incorporation assay and FACS analysis, after 48 h post-treatments. Histograms are representative of one of three separate experiments. The values represent the percentage of cells in each phase and are expressed as mean±SD. *$p<0.05$ vs vehicle treated cells; #$p<0.05$ vs THC treated cells.

Figure 4:
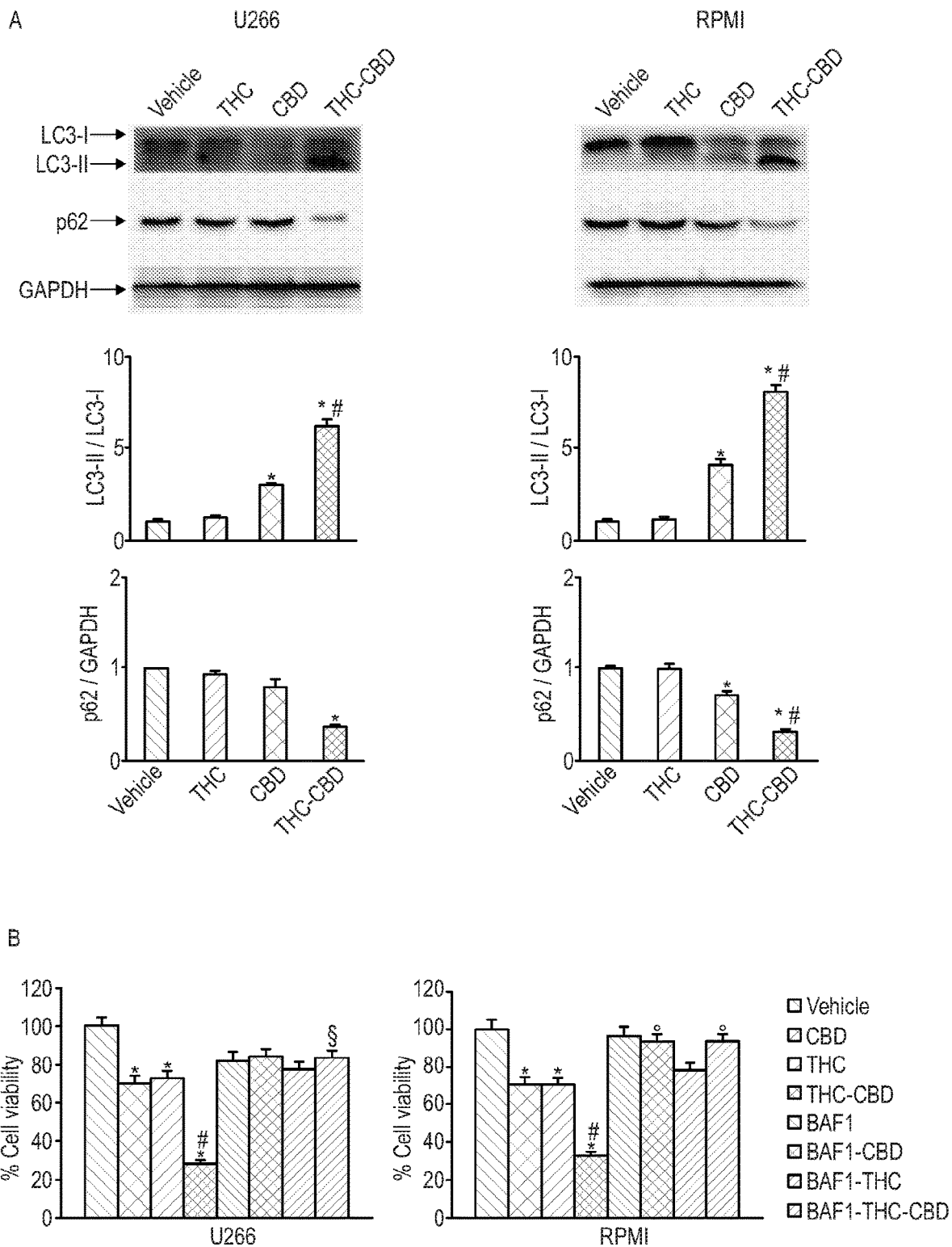
FIG. 4 shows the effect of a THC-CBD combination on autophagic-cell death in MM cell lines.

FIG. 4. (A) U266 and RPMI were treated with CBD (12.5 μM), THC (12.5 μM) alone and in combination. Lysates treated cells were separated on SDS-PAGE and probed with anti-LC3, anti-p62 and anti-GAPDH Ab. Blots are representative of one of three separate experiments. Bars represent the densitometric analysis. *p<0.01 vs vehicle and THC treated cells; #p<0.01 vs CBD or THC treated cells. (B) U266 and RPMI cell lines were pretreated with BAF1 (50 nM) for 1 h and then treated with CBD (12.5 µM), THC (12.5 µM) alone and in combination for 72 h. Data shown are expressed as mean±SD of three separate experiments. *p<0.05 vs vehicle treated cells; #p<0.05 vs THC, CBD and BAF1, alone or in combination; § p<0.05 vs THC-CBD; °p<0.05 vs THC, CBD and THC-CBD.

Figure 5:
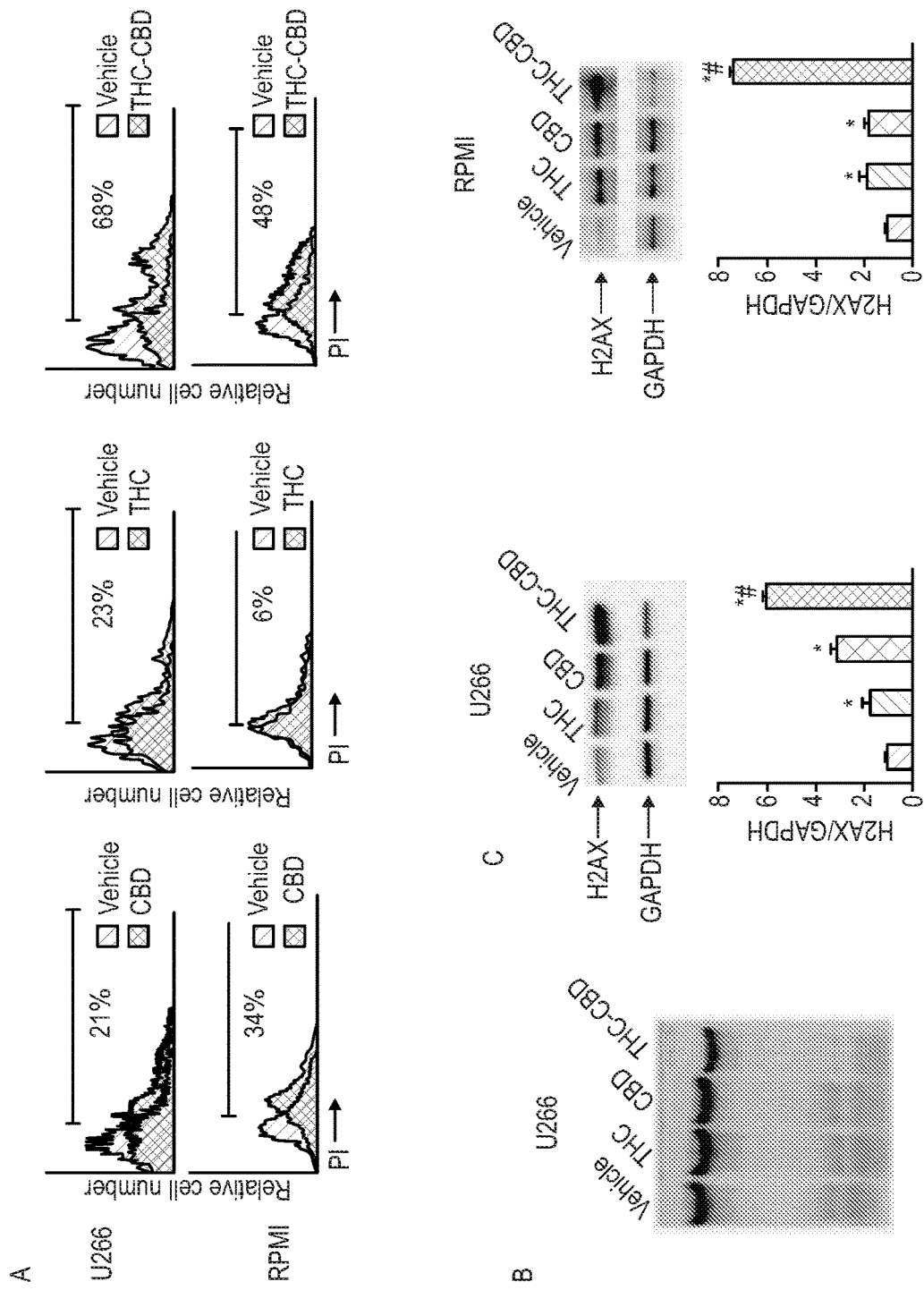
FIG. 5 shows the effect of a CBD-THC combination on necrosis.

FIG. 5. U266 and RPMI cell lines were treated for 72 h with CBD (12.5 µM), THC (12.5 µM) alone and in combination. (A) The percentage of PI positive cells were determined by FACS analysis. Histograms are representative of one of three separate experiments. (B) Representative agarose gel electrophoresis of DNA extracts obtained from U266 treated cells for the assessment of DNA fragmentation. (C) H2AX protein levels were determined by western blot analysis. H2AX densitometry values were normalized to GAPDH used as loading control. Blots are representative of one of three separate experiments. Data shown are expressed as mean±SD of three separate experiments. *p<0.05 vs vehicle treated cells; #p<0.01 vs THC or CBD treated cells.

Figure 6:
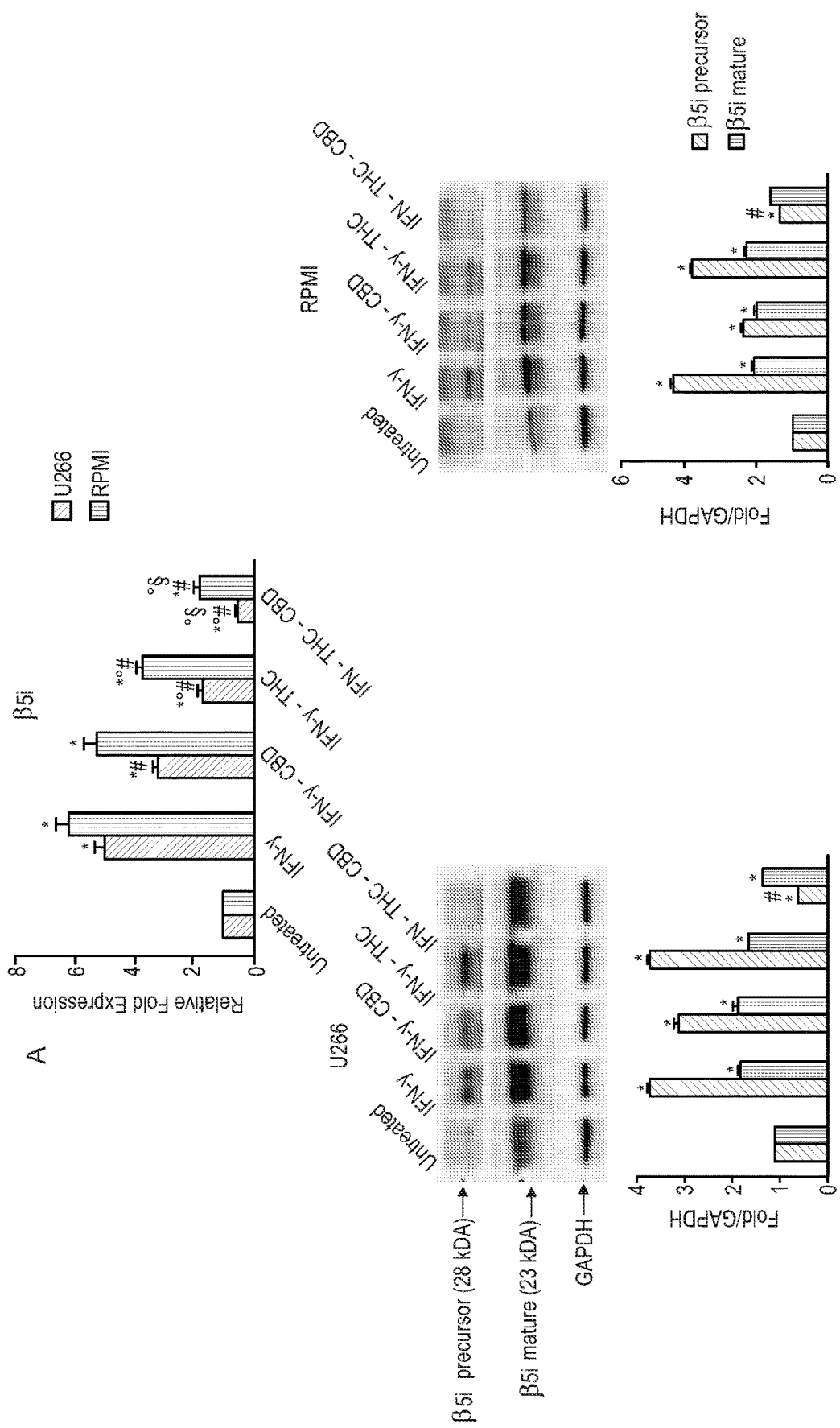
FIG. 6 shows the regulation of β5i subunit by a combination of THC-CBD in MM cell lines stimulated with IFN-γ.

FIG. 6. U266 and RPMI cells were treated with IFN-γ 100 µg/ml for 24 h. Then cells were treated with THC (12.5 µM), CBD (12.5 µM) alone and in combination for additional 24 h. (A) The β5i mRNA levels were determined by qRT-PCR. GAPDH was used for normalization. Data are expressed as relative fold with respect to vehicle treated cells used as control. Data are expressed as mean±SD. *p<0.01 vs untreated; #p<0.01 vs vehicle; °p<0.01 vs CBD; § p<0.05 vs CBD and THC alone. (B) The levels of the precursor and mature form of β5i subunit were analysed by western blot. GAPDH was used as loading control. Blots are representative of three separate experiments. Bars represent the densitometric analysis. *p<0.05 vs untreated cells; #p<0.05 vs IFN-γ treated cells.

Figure 7:
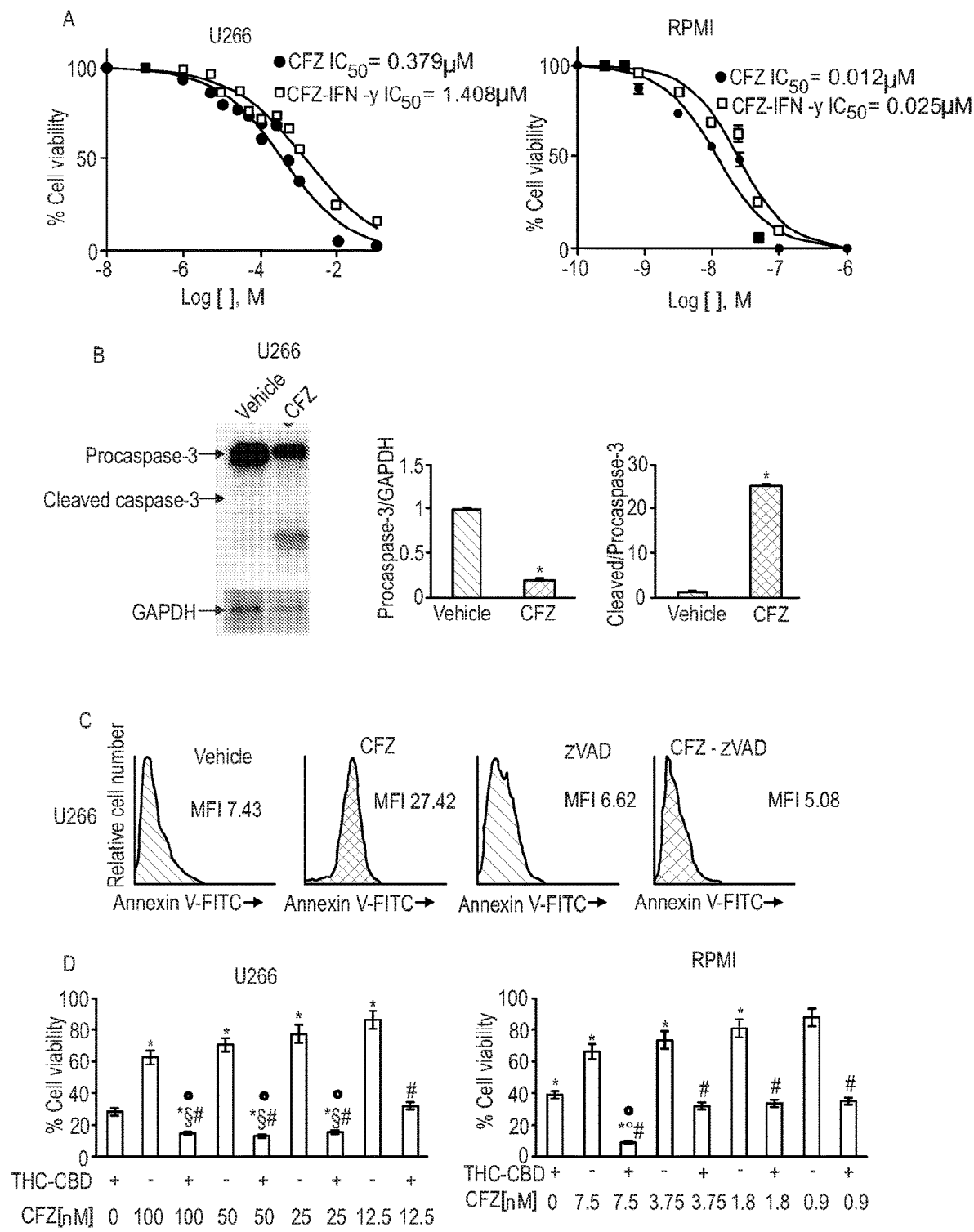
FIG. 7 shows the effect of CFZ alone or in combination with a THC-CBD combination on cell viability.

FIG. 7. (A) U266 and RPMI cell lines were cultured for 72 h with different doses of CFZ in presence or not with IFN-γ (100 µg/ml). Cell viability was determined by MTT assay. Data shown are expressed as mean±SE of three separate experiments. B) Lysates from U266 cell line treated CFZ 100 nM for 72 h were analyzed for caspase-3 protein level by western blot analysis. GAPDH protein levels were evaluated as loading control. Blots are representative of three separate experiments. Bars represent the densitometric analysis. *p<0.01 vs vehicle treated cells. (C) U266 cell lines were pretreated with 5 mM zVAD for 1 h and then treated with 100 nM CFZ for 72 h. The percentage of Annexin V positive cells were determined by FACS analysis. Histograms are representative of one of three separate experiments. MFI, mean fluorescence intensity. D) U266 and RPMI cell lines were treated with THC-CBD in combination with different doses of CFZ. Cell viability was evaluated by MTT assay. Data shown are expressed as mean±SD of three separate experiments. *p<0.01 vs THC-CBD treated cells; #p<0.01 vs CFZ alone; § p<0.01 vs THC-CBD-CFZ vs THC-CBD-CFZ (12.5 nM); °p<0.01 vs THC-CBD-CFZ (7.5 nM) vs THC-CBD-CFZ (3.75, 1.8, 0.9 nM). ✪ indicates synergism (C<1).

Figure 8:
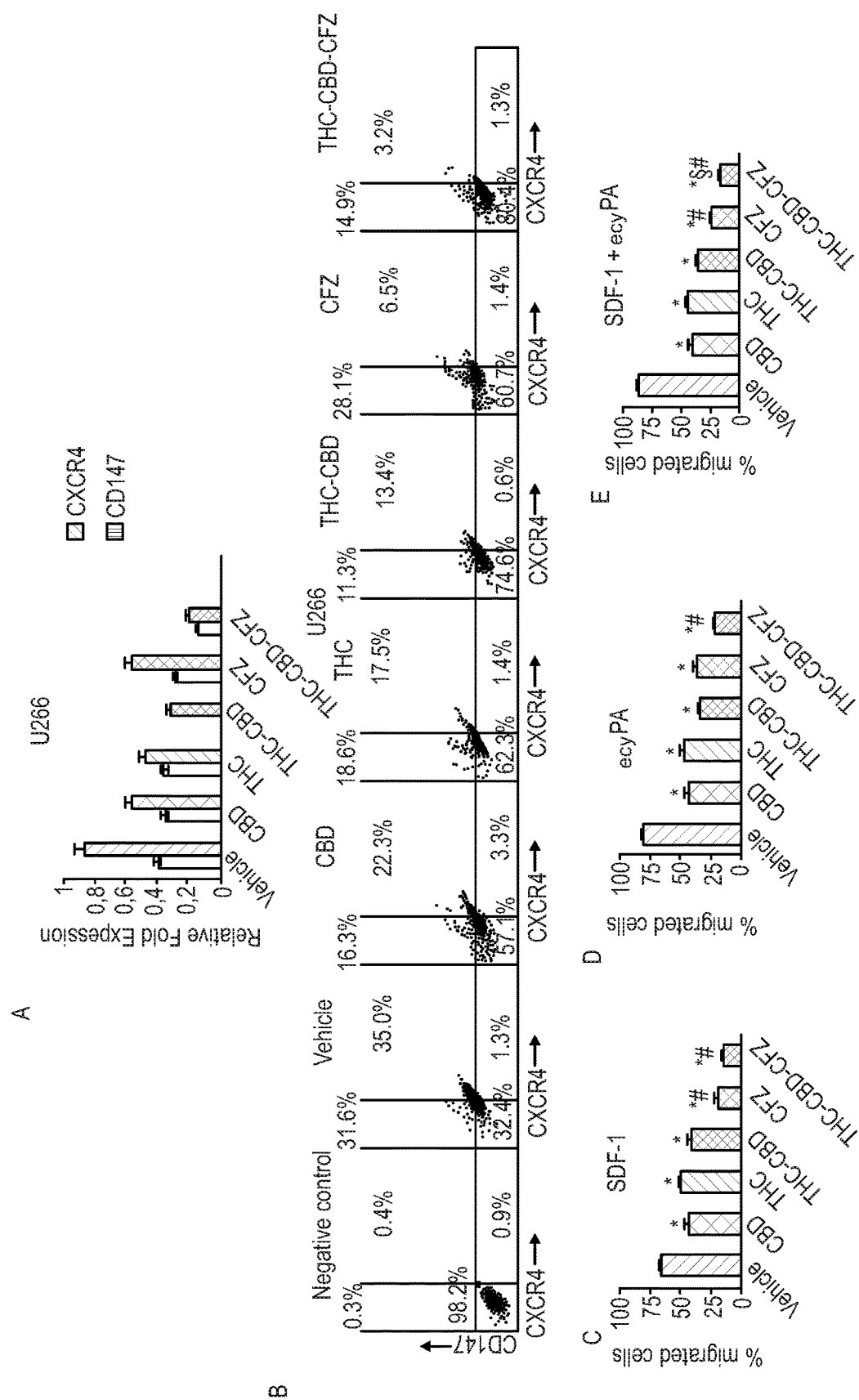
FIG. 8 shows the effect of a combination of THC, CBD and CFZ on cell migration in U266 cell line.

FIG. 8. (A) U266 cells were treated with CBD 12.5 µM, THC 12.5 µM, CFZ 100 nM alone or in combination for 24 h. CXCR4 and CD147 mRNA levels were determined by qRT-PCR. GAPDH was used for normalization. Data are expressed as relative fold with respect to vehicle treated cells used as control. Data are expressed as mean±SD. *p<0.01 vs vehicle; #p<0.01 vs THC, CBD, CFZ alone and CBD-THC; § p<0.05 vs CBD, THC; °p<0.05 vs CBD-THC. B) CXCR4 and CD147 expression was analyzed by flow cytometry on U266 cell line treated as above described. Representative dot plots illustrate the double fluorescence. Numbers represent the percentage of cells in each quadrant. Data are representative of 1 of 4 independent experiments. (C-E) Cell migration was analysed by transwell migration assays. Data represent the percentage of migrated U266 cells and are expressed as mean±SD. In C: *p<0.01 vs vehicle; #p<0.01 vs THC, CBD, CBD-THC. In D: *p<0.01 vs vehicle; #p<0.01 vs THC, CBD, THC-CBD, CFZ. In E: *p<0.01 vs vehicle; #p<0.01 vs THC, CBD, THC-CBD; § p<0.01 vs THC, CBD, THC-CBD, CFZ

DETAILED DESCRIPTION

Example 1: Efficacy of Cannabinoids on Cell Viability and Cell Migration in Multiple Myeloma Cell Lines The following example demonstrates the effects of THC alone and of a combination of THC and CBD on cell viability, survival and migration in two multiple myeloma (MM) cell lines.

The chemotherapeutic agent carfilzomib (CFZ) is a new promising immune-proteasome inhibitor that creates irreversible adducts with the β5i subunits of immune-proteasome. This compound was evaluated in combination with THC and CBD in the regulation of the expression of β5i subunits.

Materials and Methods
Cell Culture

U266 and RPM18226 (RPMI) MM cell lines were purchased from ATCC (LGC Standards, Milan, IT). Cell authentication was performed by IST (Genova, Italy). Cell lines were cultured in RPMI1640 medium (Lonza, Milan, IT) supplemented with 10% foetal bovine serum (FBS), 2 mM L-glutamine, 100 IU/ml penicillin, 100 µg/ml streptomycin and 1 mM sodium pyruvate. Cell lines were maintained at 37° C. with 5% $CO_2$ and 95% humidity.

Compounds

Pure CBD and THC used in this experiment. CBD and THC were dissolved in ethanol. AM630 and bafilomycin A1 (Tocris Bioscience, Bristol, UK) were dissolved in DMSO. z-VAD, carfilzomib (CFZ) and IFN (Sigma Aldrich, Saint Louis, Mo., USA) were dissolved in distilled water.

MTT Assay

U266 and RPMI cell lines ($4 \times 10^4$ cells/ml) were seeded in 96-well plates, in a final volume of 100 µl/well. After 1 day of incubation, compounds or vehicles were added. At least four replicates were used for each treatment.

At the indicated time point, cell viability was assessed by adding 0.8 mg/ml of 3-[4,5-dimethylthiazol-2-yl]-2,5 diphenyl tetrazolium bromide (MTT) (Sigma Aldrich) to the media. After 3 h, the plates were centrifuged, the supernatant was removed, and the pellet was solubilized with 100 µl/well DMSO.

The absorbance of the samples against a background control (medium alone) was measured at 570 nm using an ELISA reader microliter plate (BioTek Instruments, Winooski, Vt., USA). Synergistic activity of the THC-CBD combinations was determined by the isobologram and combination index (CI) methods (CompuSyn Software, ComboSyn, Inc. Paramus, N J 2007). The CI was used to express synergism (CI<1), additivity (CI=1) or antagonism (CI>1) and was calculated according to the standard isobologram equation (Chou, 2006).

Cell Cycle Analysis

U266 and RPMI cell lines ($4\times10^4$ cells/ml) were incubated with the appropriate drugs for up to 72 h. Cells were fixed for 1 h by adding ice-cold 70% ethanol and then washed with staining buffer (PBS, 2% FBS and 0.01% NaN3). The cells were treated with 100 µg/ml ribonuclease A solution (Sigma Aldrich), incubated for 30 min at 37° C., stained for 30 min at room temperature with propidium iodide (PI) 20 µg/ml (Sigma Aldrich) and analysed on a FACScan flow cytometer using CellQuest software.

Apoptosis Assay

The exposed phosphatidylserine on the U266 and RPMI cells membrane surface was detected by Annexin V staining and cytofluorimetric analysis. Briefly, 4×104 cells/ml were treated with different doses of the appropriate drugs for a maximum of 72 h. Four replicates were used for each treatment. After treatment, the cells were stained with 5 µl of Annexin V FITC (Vinci Biochem, Vinci, Italy) for 10 min at room temperature, washed once with binding buffer (10 mM N-(2-Hydroxyethyl)piperazine-N0-2-ethanesulfonic acid [HEPES]/sodium hydroxide, pH 7.4, 140 mM NaCl, 2.5 mM $CaCl_2$)) and analysed on a FACScan flow cytometer using CellQuest software.

PI Staining

After treatment with the appropriate drugs for a maximum of 72 h, 4×104 U266 and RPMI cells/ml, were incubated in a binding buffer containing 20 µg/ml PI for 10 min at room temperature. The cells were then analysed by flow cytometry using CellQuest software.

Western Blot Analysis

U266 and RPMI cell lines were lysed in buffer containing protease inhibitor cocktail (Sigma Aldrich). Lysates were resolved by sodium dodecyl sulphate polyacrylamide gel (8-14%) and transferred onto Hybond-C extra membranes (GE Healthcare, Munich, Germany). Non-specific binding sites were blocked with 5% low-fat dry milk in phosphate-buffered saline 0.1% Tween 20 for 1 h.

Blots were incubated with the primary Abs: anti-iβ5 subunit (1:1000, Cell Signalling, Denver, Colo., USA), rabbit anti-LC3 (2 µg/ml, Novus Biologicals, Littleton, Colo., USA), rabbit anti-caspase-3 (1:1000, Cell Signalling), rabbit anti-p62 (1:1000, Cell Signalling), rabbit anti-H2AX (1:1000, Cell Signalling) and mouse anti-glyceraldehydes-3-phosphate dehydrogenase (GAPDH, 1:3000, OriGene, Rockville, Md., USA) Abs overnight and then incubated with their respective HRP-conjugated anti-mouse and anti-rabbit (1:2000, Cell Signalling) Abs for 1 h. The detection was performed using the LiteAblot PLUS or the LiteAblot TURBO (EuroClone, Milano, Italy) kits, and densitometric analysis was carried out by a Chemidoc using the Quantity One software (Bio-Rad, Hercules, Calif., USA).

DNA Fragmentation Assay

Electrophoresis of DNA was performed to assess DNA fragmentation as an indicator of necrosis and apoptosis. Briefly, $4\times10^4$ cells/ml were treated with the appropriate compounds for 72 h, and the genomic DNA was extracted using a DNA extraction kit (Qiagen). The purified samples were then subjected to electrophoresis on 1.25% agarose gel, stained with ethidium bromide. Ultraviolet spectroscopy at 302 nm was used to obtain the results.

RT-PCR Analysis

Total RNA was extracted with the RNeasy Mini Kit (Qiagen), and cDNA was synthesized using the High-Capacity cDNA Archive Kit (Applied Biosystems, Foster City, Pa.) according to the manufacturer's instructions. Quantitative realtime polymerase chain reactions (qRT-PCR) for iβ5, CXCR4 and CD147 were performed using the iQ5 Multi-color Real-Time PCR Detection System (Bio-Rad, Hercules, Calif.). PCR reaction was performed with RT2SYBRGreen qPCT mastermix (QIAGEN) using 1 µl of cDNA for reaction, following the amplification protocol described in the manufacture's instruction. RT2 qPCR Primer assays (QIAGEN) were used for target gene amplification. All samples were assayed in triplicates in the same plate. Measurement of GAPDH levels was used to normalize mRNA contents, and target gene levels were calculated by the $2^{-\Delta\Delta Ct}$ method.

Cell Migration Assay

U266 and RPMI cell lines were treated with the appropriate drugs for 72 h and cell migration was evaluated by 96 wells cell migration assay (Trevigian, Md., USA) according to the manufacturer's instructions. SDF-1, eCyPA and SDF-1-eCyPA in combination were added to the bottom chamber as chemotaxis inducing agents. Data from the standard curve were used to determine the number of cells that have migrated, as well as percentage of cell migration.

Statistical Analysis

The statistical significance was determined by analysis of variance (ANOVA) or Student's t test; *, #$p<0.05$. The statistical analysis of IC50 levels was performed using Prism 5.01 (Graph Pad). Data from untreated cells were omitted because no differences were observed between vehicle-treated and untreated cells.

Results

THC and THC-CBD Combinations Induced Cytotoxicity in MM Cell Lines.

The effect of CBD in reducing cell viability has previously been demonstrated (Morelli et al. 2014) in U266 (IC50=19.8 µM) and in RPMI (IC50=22.4 µM) cell lines. We evaluated CBD in our own studies and it was found to produce a 20% decrease in cell viability in both U266 and RPMI cell lines when administered at 12.5 µM. There was no additional benefit in decrease of cell viability in either cell line from the combination of CBD with carfilzomib.

THC (up to 1 mM) was used to treat U266 and RPMI cells for 72 h and the percentage of cell viability was evaluated by MTT assay.

The results showed a dose dependent THC effect in both cell lines, with an IC50 of 39.5 µM and 30.8 µM in U266 and RPMI cells respectively (FIG. 1A).

The effects of different combinations of THC and CBD was also determined to evaluate a potential synergism between the two cannabinoids, in both cell lines.

The results demonstrated that different amounts of THC and CBD showed more effective cytotoxicity compared to THC alone (FIG. 1B).

In addition THC (25 µM and 12.5 µM) acts synergistically (CI<1) with CBD (50, 25 and 12.5 µM), inducing higher cytotoxic effects compared with single doses (FIG. 1B).

The lowest doses of 12.5 µM for CBD and 12.5 µM for THC were then used in the following experiments.

Furthermore, the cytotoxic effect of CBD and THC alone and in combination was demonstrated to be not CB2 receptors dependent, as evidenced by pre-treating MM cell lines with 20 µM AM630 (CB2 antagonist) followed by THC alone or in combination with CBD (FIG. 2).

These data additionally demonstrate that when CBD is present in an amount greater than THC there is a bigger decrease in cell viability. For example in FIG. 1B when the dose of THC used is 12.5 µM the percentage cell viability decreased from 37% to 12.5% when the amount of CBD was increased to 25 and 50 µM. Therefore ratios of 1:2 and 1:4 (THC:CBD) may be of additional benefit in the treatment of multiple myeloma.

THC-CBD Combination Induces Cell Cycle Arrest in MM Cell Lines.

The effect of CBD in blocking cell cycle in G0/G1 phase (38% in U266, 42% in RPMI) has been previously demonstrated (Morelli et al. 2014).

The role of THC alone or in combination with CBD in influencing cell cycle, in both MM cell lines was tested in these experiments. Cell cycle phases were analysed by PI staining and FACS analysis after 48 h of treatment, in both cell lines.

The results demonstrated that THC is able to induce cell accumulation in G1 phase, starting from 24 h post-treatment, accompanied by accumulation in sub-G1 phase (hypodiploid DNA) at 48 h post-treatment, compared with their respective control (FIG. 3).

The THC-CBD combination was statistically more effective in increasing G1 cell population and sub-G1 phase, at 24 h post-treatment and in augmenting cell accumulation in sub-G1 phase at 48 h, compared with THC and CBD used alone (FIG. 3).

These data suggest that THC-CBD combination is more effective than THC or CBD used as single agents in inducing cell death, in both cell lines.

THC-CBD Combination Induces Autophagic-Cell Death in MM Cell Lines.

These experiments investigated if the increase in sub-G1 cell accumulation by THC-CBD combination treatment was due to an autophagic-cell death process. Western blot analysis was used to examined the conversion of the soluble form of LC3 (LC3-1) to the lipidated and autophagosome-associated form (LC3-II), marker of autophagy activation, in THC, CBD and THC-CBD treated cells after 24 h of treatment.

It was found that CBD alone induces a slight increase of LC3-II/LC3-1 ratio, THC has no effect, while the THC-CBD combination strongly augmented the levels of the cleaved LC3-II form and the LC3-II/LC3-1 ratio, compared with single treatments (FIG. 4A).

The variation of p62 levels was also evaluated. Here the THC-CBD combination was able to strongly reduce p62 protein levels, with respect to THC or CBD alone treated cells (FIG. 4A).

The role of the autophagic pathway in THC and CBD effects was determined by pretreatment of the cells with the autophagic inhibitor bafilomycin A1 (BAF1).

An MTT assay showed that CBD and THC-CBD cytotoxic effects were reversed by the pre-treatment with BAF1 (FIG. 4B).

PI staining and FACS analysis were also used to show that the THC-CBD combination induced higher necrotic cell death compared with THC or CBD alone, at 48 h post-treatments, in both MM cell lines (FIG. 5A).

Furthermore, it was also demonstrated that augmented levels of damaged DNA after treatment with the THC-CBD combination with respect to the single treatment as demonstrated by genomic DNA fragmentation analysis (FIG. 5B).

The presence of γ-H2AX (H2AX), a phosphorylated variant of histone 2A that is associated with DNA double-strand breaks was investigated. Immunoblots showed that THC or CBD alone in both cell lines were able to induce an increase levels of the phosphorylated form of H2AX (FIG. 5C) at 24 h post-treatments, and the THC-CBD combination further improved the H2AX levels respect to the single treatments, in both MM cell lines (FIG. 5C).

Effect of THC-CBD in Regulating the β5i Subunit in MM Cell Lines.

The potential role of the combination of THC-CBD in regulating the β5i subunit was investigated. U266 and RPMI cell lines were treated with CBD and THC, after 24 h exposure to IFN-γ (100 U/ml).

Using qRT-PCR, the THC-CBD combination was shown to strongly reduce the β5i increased expression level induced by IFN-γ, while low effects were observed with single CBD or THC treatments respect to IFN-γ alone (FIG. 6A).

At protein levels, the expression of the precursor and mature form of β5i was examined by western blot analysis. Results confirmed β5i mRNA levels showing that the administration of IFN-γ increases both precursor and mature form of β5i in MM treated compared with non-treated cells. Moreover, THC or CBD alone had low efficacy in reducing β5i, while the THC-CBD combination impaired the expression of both forms, in both cell lines.

THC-CBD Combination Synergizes with CFZ in Reducing Cell Viability in MM Cell Lines.

CFZ reduced cell viability, U266 and RPMI cell lines in the presence or absence of IFN-γ, as evaluated by MTT assay 72 h post-treatment (data not shown).

The effect of CFZ plus the THC-CBD combination on MM cell viability was evaluated. RPMI and U266 cells were treated with different doses of CFZ (0.9 up to 7.5 nM doses for RPMI, 12.5 up to 100 nM doses for U266) in combination with THC-CBD. The results showed that most of the combinations strongly reduced cell viability compared with single treatments in both cell lines (FIG. 7D). Moreover, we evidenced that the THC-CBD combination acts synergistically (CI<1) with CFZ (50, 25 and 12.5 nM in U266; 7.5 nM in RPMI) to induce cytotoxic effects.

THC-CBD in Combination with CFZ Inhibits Cell Migration in MM Cell Lines.

The expression of CXCR4 and CD147 in U266 and RPMI cell lines by qRT-PCR and FACS analysis was evaluated. The qRT-PCR results showed that CXCR4 is expressed, although at lower levels respect CD147, in both RPMI and U266 cell lines (FIG. 8A). FACS analysis confirmed the qRT-PCR data, since 95% and 41% of RPMI and 66.6% and 35% of U266 cell population express CD147 and CXCR4. All CXCR4+ RPMI and U266 cells were CD147+ (FIG. 8B).

The effect of CBD, THC and CFZ alone or in combination, in regulating CXCR4 and CD147 expression, in both MM cell lines was tested.

Cells were treated with a single dose of compounds alone or in combination for 24 h and mRNA transcripts and protein levels were analyzed by qRT-PCR and FACS analysis. qRT-PCR showed that CXCR4 and CD147 transcript levels decrease, and that the combination CBD-THC plus CFZ was most effective in reducing CXCR4 and CD147 mRNA expression in both MM cell lines (FIG. 8A).

The qRT-PCR results were then confirmed by FACS analysis. A substantial decrease of both CXCR4+ and CD147+ and CXCR4+CD147+ cells, compared with the respective control cells was observed in U266 and RPMI MM cell lines (FIG. 8B), with the THC-CBD combination plus CFZ being more effective in reducing the percentage of CXCR4+CD147+ and CD147+ cell phenotype.

To further investigate this effect, U266 and RPMI cells were treated for 24 h with the appropriate dose of CBD, THC and CFZ alone and in combination and then cell migration was measured.

The results showed that CBD, THC and CFZ both in single and in combination, reduced the SDF-1-, eCyPA- and SDF-1/eCyPA-mediated chemotaxis, compared with vehicle-treated cells (FIG. 8C).

These data suggest that CBD, THC and CFZ alone and in combination reduce the expression of CXCR4 and CD147 chemotactic receptors related to SDF-1-, eCyPA- and SDF-1/eCyPA-mediated chemotaxis in MM cell lines.

CONCLUSIONS

Over the last twenty years the antitumor effects of cannabinoids have been proved in different human cancer cell lines and in vivo preclinical models (Velasco et al. 2016). In multiple myeloma, it has been demonstrated that CBD reduced cell proliferation and induced necrotic cell death (Morelli et al., 2014).

The data presented in Example 1 above demonstrates that a THC-CBD combination is statistically more effective in reducing multiple myeloma cell viability and migration.

In addition the THC-CBD combination when combined with the proteasome inhibitor carfilzomib demonstrates statistically significant effects in both cell viability and cell migration, evidencing a synergy between all three drugs.

The use of combination anti-cancer therapy is an innovative therapeutic strategy. The purpose of combining drugs in therapeutic regimens is to achieve an overall effect that is greater than the sum of the individual effects of each agent.

At present there has been no data published on the ability of cannabinoids to reduce cell migration in multiple myeloma. A migration assay was performed and demonstrated that the triple combination of THC-CBD and CFZ was able to strongly reduce the migration of cells in both cell lines.

Due to the nature of the disease the ability of the combination of THC and CBD and the triple therapy of THC, CBD and CFZ to inhibit cell migration suggests a very important role. Such an ability to stop the MM cells from migrating to other areas of the body not only means that the disease will not progress as quickly but additionally means there is less likelihood for the disease to relapse.

In conclusion, these data demonstrate that the combination of THC and CBD with or without the proteasome inhibitor carfilzomib is effective in reducing both the viability and migration of multiple myeloma cells. A further benefit of the triple therapy would mean that the chemotherapeutic drugs dose could be reduced without a loss of activity.

REFERENCES

Chou T C. Theoretical basis, experimental design, and computerized simulation of synergism and antagonism in drug combination studies. Pharmacol Rev. 2006; 58(3): 621-81.

Kuhn D J, Chen Q, Voorhees P M, Strader J S, Shenk K D, Sun C M, Demo S D, Bennett M K, van Leeuwen F W, Chanan-Khan A A, Orlowski R Z. Potent activity of carfilzomib, a novel, irreversible inhibitor of the ubiquitin-proteasome pathway, against preclinical models of multiple myeloma. Blood. 2007; 110(9):3281-90.

Morelli M B, Offidani M, Alesiani F, Discepoli G, Liberati S, Olivieri A, Santoni M, Santoni G, Leoni P, Nabissi M. The effects of cannabidiol and its synergism with bortezomib in multiple myeloma cell lines. A role for transient receptor potential vanilloid type-2. Int J Cancer. 2014; 134(11):2534-46.

Morelli M B, Offidani M, Alesiani F, Discepoli G, Liberati S, Olivieri A, Santoni M, Santoni G, Leoni P, Nabissi M. The effects of cannabidiol and its synergism with bortezomib in multiple myeloma cell lines. A role for transient receptor potential vanilloid type-2. Int J Cancer. 2014; 134(11):2534-46.

Raab M S, Podar K, Breitkreutz I, Richardson P G, Anderson K C. Multiple myeloma. Lancet. 2009; 374(9686): 324-39.

Velasco G, Sánchez C, Guzmán M. Anticancer mechanisms of cannabinoids. Curr Oncol. 2016; 23(2):S23-32.

The invention claimed is:

1. A method for treating multiple myeloma comprising administering to a subject in need thereof a therapeutically effective amount of a *cannabis* extract and a proteasome inhibitor,
    wherein the *cannabis* extract comprises the cannabinoids tetrahydrocannabinol (THC) and cannabidiol (CBD), wherein THC and CBD are present at greater than 98% (w/w) in the extract, and
    wherein the proteasome inhibitor is bortezomib, carfilzomib or ixazomib.

2. The method of claim 1, further comprising administering one or more additional medications.

3. The method of claim 1, wherein the proteasome inhibitor is bortezomib or carfilzomib.

4. The method of claim 1, wherein the proteasome inhibitor is carfilzomib.

5. The method of claim 1, wherein the proteasome inhibitor is administered at a dose that is reduced relative to a dose of proteasome inhibitor administered prior to treatment with the THC and CBD.

6. The method of claim 1, wherein the proteasome inhibitor is administered at a dose that is reduced relative to a therapeutically effective dose of the proteasome inhibitor for the subject without treatment with the THC and CBD.

7. The method of claim 1, wherein the proteasome inhibitor is administered at a dose of less than 27 mg/m$^2$ IV.

8. The method of claim 1, wherein the proteasome inhibitor is administered at a dose of less than 20 mg/m$^2$ IV.

9. The method of claim 1, wherein the THC, CBD, or both are administered at a dose of from 0.1 to 1000 mg/kg/day.

10. The method of claim 1, wherein the THC and CBD are present in a ratio of from 99:1 to 1:99 (THC:CBD).

11. The method of claim 1, wherein the THC and CBD are present in a ratio of from 10:1 to 1:10 (THC:CBD).

12. The method of claim 1, wherein the THC and CBD are present in a ratio of from 5:1 to 1:5 (THC:CBD).

13. The method of claim 1, wherein the THC and CBD are present in a ratio of approximately 1:1 (THC:CBD).

14. The method of claim 3, wherein the proteasome inhibitor is ixazomib.

15. The method of claim 1, wherein treating reduces chemotaxis of multiple myeloma cells to cells expressing SDF-1, eCypA, or both.

16. The method of claim 4, wherein treating reduces chemotaxis of multiple myeloma cells to cells expressing SDF-1, eCypA, or both.

* * * * *

UNITED STATES PATENT AND TRADEMARK OFFICE
CERTIFICATE OF CORRECTION

PATENT NO. : 11,065,227 B2
APPLICATION NO. : 16/328209
DATED : July 20, 2021
INVENTOR(S) : Colin Stott et al.

Page 1 of 1

It is certified that error appears in the above-identified patent and that said Letters Patent is hereby corrected as shown below:

In the Claims

At Column 14, Claim number 4, Line number 31:
"4. The method of claim 1, wherein the proteasome inhibi-"
Should read:
-- 4. The method of claim 3, wherein the proteasome inhibi- --

Signed and Sealed this
Fifth Day of July, 2022

Katherine Kelly Vidal
*Director of the United States Patent and Trademark Office*